United States Patent
Otte et al.

(10) Patent No.: US 9,468,471 B2
(45) Date of Patent: Oct. 18, 2016

(54) TRANSVERSE COUPLER ADJUSTER SPINAL CORRECTION SYSTEMS AND METHODS

(71) Applicant: K2M, Inc., Leesburg, VA (US)

(72) Inventors: John F. Otte, Minneapolis, MN (US); Thomas J. Gisel, Chaska, MN (US); Matthew S. Stenulson, Hopkins, MN (US)

(73) Assignee: K2M, Inc., Leesburg, VA (US)

( * ) Notice: Subject to any disclaimer, the term of this patent is extended or adjusted under 35 U.S.C. 154(b) by 339 days.

(21) Appl. No.: 14/029,620

(22) Filed: Sep. 17, 2013

(65) Prior Publication Data

US 2015/0080954 A1  Mar. 19, 2015

(51) Int. Cl.
*A61B 17/70* (2006.01)

(52) U.S. Cl.
CPC ....... *A61B 17/7052* (2013.01); *A61B 17/7049* (2013.01)

(58) Field of Classification Search
CPC ............ A61B 17/7049; A61B 17/705; A61B 17/7052
See application file for complete search history.

(56) References Cited

U.S. PATENT DOCUMENTS

| | | |
|---|---|---|
| 2,774,350 A | 12/1956 | Cleveland, Jr. |
| 3,242,922 A | 3/1966 | Thomas |
| 3,352,226 A | 11/1967 | Nelsen |
| 3,648,691 A | 3/1972 | Lumb et al. |
| 3,693,616 A | 9/1972 | Roaf et al. |
| 3,865,105 A | 2/1975 | Lode |
| 4,024,588 A | 5/1977 | Janssen et al. |
| 4,078,559 A | 3/1978 | Nissinen |
| 4,257,409 A | 3/1981 | Bacal et al. |
| 4,269,178 A | 5/1981 | Keene |
| 4,274,401 A | 6/1981 | Miskew |
| 4,355,645 A | 10/1982 | Mitani et al. |
| 4,361,141 A | 11/1982 | Tanner |
| 4,369,769 A | 1/1983 | Edwards |
| 4,404,967 A | 9/1983 | Bacal et al. |
| 4,411,259 A | 10/1983 | Drummond |
| 4,411,545 A | 10/1983 | Roberge |
| 4,448,191 A | 5/1984 | Rodnyansky et al. |
| 4,505,268 A | 3/1985 | Sgandurra |
| 4,554,914 A | 11/1985 | Kapp et al. |
| 4,573,454 A | 3/1986 | Hoffman |

(Continued)

FOREIGN PATENT DOCUMENTS

| | | |
|---|---|---|
| DE | 2644735 A1 | 4/1977 |
| DE | 2845647 A1 | 5/1980 |

(Continued)

OTHER PUBLICATIONS

International Search Report and Written Opinion issued in PCT/US2012/040493, mailed Aug. 21, 2012, 15 pages.

(Continued)

*Primary Examiner* — Eduardo C Robert
*Assistant Examiner* — Julianna N Harvey
(74) *Attorney, Agent, or Firm* — Carter, DeLuca, Farrell & Schmidt, LLP

(57) ABSTRACT

Systems, devices, and associated methods for correcting and stabilizing spinal column deformities that promote ease of use and surgical technique, help minimize attachment anchor sites, facilitate use of straight or contoured rods, and/or help promote a more natural, physiologic motion of the spinal column during and/or after correction.

17 Claims, 12 Drawing Sheets

(56) References Cited

U.S. PATENT DOCUMENTS

| | | |
|---|---|---|
| 4,604,995 A | 8/1986 | Stephens et al. |
| 4,611,581 A | 9/1986 | Steffee |
| 4,611,582 A | 9/1986 | Duff |
| 4,634,445 A | 1/1987 | Helal |
| 4,648,388 A | 3/1987 | Steffee |
| 4,653,481 A | 3/1987 | Howland et al. |
| 4,658,809 A | 4/1987 | Ulrich et al. |
| 4,697,582 A | 10/1987 | William |
| 4,738,251 A | 4/1988 | Plaza |
| 4,773,402 A | 9/1988 | Asher et al. |
| 4,805,602 A | 2/1989 | Puno et al. |
| 4,815,453 A | 3/1989 | Cotrel |
| 4,827,918 A | 5/1989 | Olerud |
| 4,854,311 A | 8/1989 | Steffee |
| 4,931,055 A | 6/1990 | Bumpus et al. |
| 4,936,848 A | 6/1990 | Bagby |
| 5,000,166 A | 3/1991 | Karpf |
| 5,005,562 A | 4/1991 | Cotrel |
| 5,011,484 A | 4/1991 | Breard |
| 5,030,220 A | 7/1991 | Howland |
| 5,042,982 A | 8/1991 | Harms et al. |
| 5,084,049 A | 1/1992 | Asher et al. |
| 5,092,866 A | 3/1992 | Breard et al. |
| 5,092,867 A | 3/1992 | Harms et al. |
| 5,127,912 A | 7/1992 | Ray et al. |
| 5,129,900 A | 7/1992 | Asher et al. |
| 5,133,716 A | 7/1992 | Plaza |
| 5,147,363 A | 9/1992 | Harle |
| 5,176,679 A | 1/1993 | Lin |
| 5,176,680 A | 1/1993 | Vignaud et al. |
| 5,181,917 A | 1/1993 | Rogozinski |
| 5,190,543 A | 3/1993 | Schlapfer |
| 5,196,014 A | 3/1993 | Lin |
| 5,207,678 A | 5/1993 | Harms et al. |
| 5,209,752 A | 5/1993 | Ashman et al. |
| 5,219,349 A | 6/1993 | Krag et al. |
| 5,242,443 A | 9/1993 | Kambin |
| 5,254,118 A | 10/1993 | Mirkovic |
| 5,257,994 A | 11/1993 | Lin |
| 5,259,398 A | 11/1993 | Vrespa |
| 5,282,862 A | 2/1994 | Baker et al. |
| 5,306,275 A | 4/1994 | Bryan |
| 5,312,404 A | 5/1994 | Asher et al. |
| 5,312,410 A | 5/1994 | Miller et al. |
| 5,312,420 A | 5/1994 | Toso et al. |
| 5,330,473 A | 7/1994 | Howland |
| 5,330,474 A | 7/1994 | Lin |
| 5,352,226 A | 10/1994 | Lin |
| 5,360,431 A | 11/1994 | Puno et al. |
| 5,366,455 A | 11/1994 | Dove et al. |
| 5,368,594 A | 11/1994 | Martin et al. |
| 5,380,323 A | 1/1995 | Howland |
| 5,380,325 A | 1/1995 | Lahille et al. |
| 5,382,248 A | 1/1995 | Jacobson et al. |
| 5,387,212 A | 2/1995 | Yuan et al. |
| 5,387,213 A | 2/1995 | Breard et al. |
| 5,391,168 A | 2/1995 | Sanders et al. |
| 5,397,363 A | 3/1995 | Gelbard |
| 5,413,576 A | 5/1995 | Rivard |
| 5,436,542 A | 7/1995 | Petelin et al. |
| 5,437,669 A | 8/1995 | Yuan et al. |
| 5,437,671 A | 8/1995 | Lozier et al. |
| 5,456,722 A | 10/1995 | McLeod et al. |
| 5,466,238 A | 11/1995 | Lin |
| 5,470,333 A | 11/1995 | Ray |
| 5,480,440 A | 1/1996 | Kambin |
| 5,486,174 A | 1/1996 | Fournet-Fayard et al. |
| 5,487,744 A | 1/1996 | Howland |
| 5,490,851 A | 2/1996 | Nenov et al. |
| 5,496,318 A | 3/1996 | Howland et al. |
| 5,498,262 A | 3/1996 | Bryan |
| 5,501,684 A | 3/1996 | Schlapfer et al. |
| 5,520,688 A | 5/1996 | Lin |
| 5,527,314 A | 6/1996 | Brumfield et al. |
| 5,534,002 A | 7/1996 | Brumfield et al. |
| 5,540,689 A | 7/1996 | Sanders et al. |
| 5,544,993 A | 8/1996 | Harle |
| 5,549,679 A | 8/1996 | Kuslich |
| 5,562,660 A | 10/1996 | Grob |
| 5,562,662 A | 10/1996 | Brumfield et al. |
| 5,569,246 A | 10/1996 | Ojima et al. |
| 5,571,191 A | 11/1996 | Fitz |
| 5,575,791 A | 11/1996 | Lin |
| 5,584,626 A | 12/1996 | Assmundson |
| 5,586,983 A | 12/1996 | Sanders et al. |
| 5,591,165 A | 1/1997 | Jackson |
| 5,601,554 A | 2/1997 | Howland et al. |
| 5,609,592 A | 3/1997 | Brumfield et al. |
| 5,611,800 A | 3/1997 | Davis et al. |
| 5,620,443 A | 4/1997 | Gertzbein et al. |
| 5,630,816 A | 5/1997 | Kambin |
| 5,643,259 A | 7/1997 | Sasso et al. |
| 5,645,599 A | 7/1997 | Samani |
| 5,649,926 A | 7/1997 | Howland |
| 5,658,284 A | 8/1997 | Sebastian et al. |
| 5,672,175 A | 9/1997 | Martin |
| 5,676,703 A | 10/1997 | Gelbard |
| 5,702,395 A | 12/1997 | Hopf |
| 5,702,399 A | 12/1997 | Kilpela et al. |
| 5,702,452 A | 12/1997 | Argenson et al. |
| 5,704,936 A | 1/1998 | Mazel |
| 5,713,898 A | 2/1998 | Stucker et al. |
| 5,716,355 A | 2/1998 | Jackson et al. |
| 5,725,582 A | 3/1998 | Bevan et al. |
| 5,728,097 A | 3/1998 | Mathews |
| 5,733,284 A | 3/1998 | Martin |
| 5,735,852 A | 4/1998 | Amrein et al. |
| 5,782,831 A | 7/1998 | Sherman et al. |
| 5,797,910 A | 8/1998 | Martin |
| 5,810,817 A | 9/1998 | Roussouly et al. |
| 5,810,819 A | 9/1998 | Errico et al. |
| 5,814,046 A | 9/1998 | Hopf |
| 5,885,285 A | 3/1999 | Simonson |
| 5,891,145 A | 4/1999 | Morrison et al. |
| 5,902,305 A | 5/1999 | Beger et al. |
| 5,910,142 A | 6/1999 | Tatar |
| 5,928,232 A | 7/1999 | Howland et al. |
| 5,938,663 A * | 8/1999 | Petreto ............... A61B 17/7041 606/278 |
| 5,947,967 A | 9/1999 | Barker |
| 5,964,769 A | 10/1999 | Wagner et al. |
| 5,976,135 A | 11/1999 | Sherman et al. |
| 5,980,521 A | 11/1999 | Montague et al. |
| 5,984,924 A * | 11/1999 | Asher ............... A61B 17/7007 606/264 |
| 5,989,256 A | 11/1999 | Kuslich et al. |
| 6,015,409 A | 1/2000 | Jackson |
| 6,033,412 A | 3/2000 | Losken et al. |
| 6,039,738 A | 3/2000 | Sanders et al. |
| 6,053,921 A | 4/2000 | Wagner et al. |
| 6,066,140 A | 5/2000 | Gertzbein et al. |
| 6,077,268 A | 6/2000 | Farris et al. |
| 6,080,156 A | 6/2000 | Asher et al. |
| 6,083,224 A | 7/2000 | Gertzbein et al. |
| 6,086,590 A | 7/2000 | Margulies et al. |
| 6,101,678 A | 8/2000 | Malloy et al. |
| 6,110,173 A | 8/2000 | Thomas, Jr. |
| 6,123,706 A | 9/2000 | Lange |
| 6,132,431 A | 10/2000 | Nilsson et al. |
| 6,132,464 A | 10/2000 | Martin |
| 6,136,000 A | 10/2000 | Louis et al. |
| 6,176,861 B1 | 1/2001 | Bernstein et al. |
| 6,231,575 B1 * | 5/2001 | Krag ............... A61B 17/7041 606/264 |
| 6,248,106 B1 | 6/2001 | Ferree |
| 6,251,111 B1 | 6/2001 | Barker et al. |
| 6,254,603 B1 | 7/2001 | Gertzbein et al. |
| 6,261,288 B1 | 7/2001 | Jackson |
| 6,264,658 B1 | 7/2001 | Lee et al. |
| 6,273,914 B1 | 8/2001 | Papas |
| 6,277,120 B1 | 8/2001 | Lawson |
| 6,283,967 B1 | 9/2001 | Troxell et al. |
| 6,293,949 B1 | 9/2001 | Justis et al. |
| 6,296,643 B1 | 10/2001 | Hopf et al. |

(56) References Cited

U.S. PATENT DOCUMENTS

| | | |
|---|---|---|
| 6,299,613 B1 | 10/2001 | Ogilvie et al. |
| 6,325,805 B1 | 12/2001 | Ogilvie et al. |
| 6,328,739 B1 | 12/2001 | Liu et al. |
| 6,358,254 B1 | 3/2002 | Anderson |
| 6,364,883 B1 | 4/2002 | Santilli |
| 6,364,885 B1 | 4/2002 | Kilpela et al. |
| 6,391,030 B1 | 5/2002 | Wagner et al. |
| 6,402,749 B1 | 6/2002 | Ashman |
| 6,402,752 B2 | 6/2002 | Schaffler-Wachter et al. |
| 6,419,703 B1 | 7/2002 | Fallin et al. |
| 6,423,065 B2 | 7/2002 | Ferree |
| 6,451,019 B1 | 9/2002 | Zucherman et al. |
| 6,458,131 B1 | 10/2002 | Ray |
| 6,471,704 B2 | 10/2002 | Gertzbein et al. |
| 6,488,683 B2 | 12/2002 | Lieberman |
| 6,514,255 B1 | 2/2003 | Ferree |
| 6,520,962 B1 | 2/2003 | Taylor et al. |
| 6,537,276 B2 | 3/2003 | Metz Stavenhagen |
| 6,547,789 B1 | 4/2003 | Ventre et al. |
| 6,551,320 B2 | 4/2003 | Lieberman |
| 6,554,831 B1 | 4/2003 | Rivard et al. |
| 6,562,038 B1 | 5/2003 | Morrison |
| 6,565,569 B1 | 5/2003 | Assaker et al. |
| 6,565,605 B2 | 5/2003 | Goble et al. |
| 6,569,164 B1 | 5/2003 | Assaker et al. |
| 6,579,292 B2 | 6/2003 | Taylor |
| 6,579,319 B2 | 6/2003 | Goble et al. |
| 6,582,433 B2 | 6/2003 | Yun |
| 6,585,738 B1 | 7/2003 | Mangione et al. |
| 6,589,243 B1 | 7/2003 | Viart et al. |
| 6,602,254 B2 | 8/2003 | Gertzbein et al. |
| 6,602,818 B2 | 8/2003 | Choi et al. |
| 6,610,091 B1 | 8/2003 | Reiley |
| 6,616,669 B2 | 9/2003 | Ogilvie et al. |
| 6,623,484 B2 | 9/2003 | Betz et al. |
| 6,626,906 B1 | 9/2003 | Young |
| 6,626,909 B2 | 9/2003 | Chin |
| 6,641,585 B2 | 11/2003 | Sato et al. |
| 6,645,207 B2 | 11/2003 | Dixon et al. |
| 6,651,320 B1 | 11/2003 | Yagi et al. |
| 6,656,185 B2 | 12/2003 | Gleason et al. |
| 6,669,729 B2 | 12/2003 | Chin |
| 6,682,532 B2 | 1/2004 | Johnson et al. |
| 6,682,533 B1 | 1/2004 | Dinsdale et al. |
| 6,685,705 B1 | 2/2004 | Taylor |
| 6,689,133 B2 | 2/2004 | Morrison et al. |
| 6,709,435 B2 | 3/2004 | Lin |
| 6,736,817 B2 | 5/2004 | Troxell et al. |
| 6,749,612 B1 | 6/2004 | Conchy et al. |
| 6,755,828 B2 | 6/2004 | Shevtsov et al. |
| 6,773,437 B2 | 8/2004 | Ogilvie et al. |
| 6,802,844 B2 | 10/2004 | Ferree |
| 6,811,567 B2 | 11/2004 | Reiley |
| 6,835,207 B2 | 12/2004 | Zacouto et al. |
| 6,840,127 B2 | 1/2005 | Moran |
| 6,860,884 B2 | 3/2005 | Shirado et al. |
| 6,887,241 B1 | 5/2005 | McBride et al. |
| 6,902,580 B2 | 6/2005 | Fallin et al. |
| 6,946,000 B2 | 9/2005 | Senegas et al. |
| 6,966,910 B2 | 11/2005 | Ritland |
| 6,966,930 B2 | 11/2005 | Arnin et al. |
| 6,974,478 B2 | 12/2005 | Reiley et al. |
| 6,986,771 B2 | 1/2006 | Paul et al. |
| 7,008,423 B2 | 3/2006 | Assaker et al. |
| 7,018,379 B2 | 3/2006 | Drewry et al. |
| 7,029,475 B2 | 4/2006 | Panjabi |
| 7,041,136 B2 | 5/2006 | Goble et al. |
| 7,048,736 B2 | 5/2006 | Robinson et al. |
| 7,051,451 B2 | 5/2006 | Augostino et al. |
| 7,074,237 B2 | 7/2006 | Goble et al. |
| 7,083,621 B2 | 8/2006 | Shaolian et al. |
| 7,087,056 B2 | 8/2006 | Vaughan |
| 7,090,698 B2 | 8/2006 | Goble et al. |
| 7,104,992 B2 | 9/2006 | Bailey |
| RE39,325 E | 10/2006 | Bryan |
| 7,128,743 B2 | 10/2006 | Metz Stavenhagen |
| 7,137,986 B2 | 11/2006 | Troxell et al. |
| 7,160,312 B2 | 1/2007 | Saadat |
| 7,220,262 B1 | 5/2007 | Hynes |
| 7,261,714 B2 | 8/2007 | Richelsoph |
| 7,270,665 B2 | 9/2007 | Morrison et al. |
| 7,290,347 B2 | 11/2007 | Augostino et al. |
| 7,294,129 B2 | 11/2007 | Hawkins et al. |
| 7,316,684 B1 | 1/2008 | Baccelli et al. |
| 7,335,203 B2 | 2/2008 | Winslow et al. |
| 7,338,490 B2 | 3/2008 | Ogilvie et al. |
| 7,344,539 B2 | 3/2008 | Serhan et al. |
| 7,361,196 B2 | 4/2008 | Fallin et al. |
| 7,367,978 B2 | 5/2008 | Drewry et al. |
| 7,406,775 B2 | 8/2008 | Funk et al. |
| 7,445,635 B2 | 11/2008 | Fallin et al. |
| 7,473,267 B2 | 1/2009 | Nguyen et al. |
| 7,473,269 B1 | 1/2009 | Hynes |
| 7,481,828 B2 | 1/2009 | Mazda et al. |
| 7,507,242 B2 | 3/2009 | Triplett et al. |
| 7,524,324 B2 | 4/2009 | Winslow et al. |
| 7,566,345 B1 | 7/2009 | Fallin et al. |
| 7,588,578 B2 | 9/2009 | Triplett et al. |
| 7,588,590 B2 | 9/2009 | Chervitz et al. |
| 7,591,836 B2 | 9/2009 | Dick et al. |
| 7,594,924 B2 | 9/2009 | Albert et al. |
| 7,611,526 B2 | 11/2009 | Carl et al. |
| 7,618,453 B2 | 11/2009 | Goble et al. |
| 7,618,455 B2 | 11/2009 | Goble et al. |
| 7,621,955 B2 | 11/2009 | Goble et al. |
| 7,648,521 B2 | 1/2010 | Hestad |
| 7,658,753 B2 | 2/2010 | Carl et al. |
| 7,674,293 B2 | 3/2010 | Kuiper et al. |
| 7,678,136 B2 | 3/2010 | Doubler et al. |
| 7,691,145 B2 | 4/2010 | Reiley et al. |
| 7,708,762 B2 | 5/2010 | McCarthy et al. |
| 7,717,940 B2 | 5/2010 | Woods et al. |
| 7,717,942 B2 | 5/2010 | Schumacher |
| 7,722,647 B1 | 5/2010 | Wang et al. |
| 7,722,648 B2 | 5/2010 | Drewry et al. |
| 7,753,937 B2 | 7/2010 | Chervitz et al. |
| 7,758,581 B2 | 7/2010 | Chervitz et al. |
| 7,771,474 B2 | 8/2010 | Cordaro |
| 7,794,476 B2 | 9/2010 | Wisnewski |
| 7,794,478 B2 | 9/2010 | Nilsson |
| 7,799,054 B2 | 9/2010 | Kwak et al. |
| 7,819,902 B2 | 10/2010 | Abdelgany et al. |
| 7,833,252 B2 | 11/2010 | Justis et al. |
| 7,837,714 B2 | 11/2010 | Drewry et al. |
| 7,842,071 B2 | 11/2010 | Hawkes |
| 7,862,586 B2 | 1/2011 | Malek |
| 7,896,906 B2 | 3/2011 | Kwak et al. |
| 7,918,876 B2 | 4/2011 | Mueller et al. |
| 7,927,359 B2 | 4/2011 | Trautwein et al. |
| 7,931,676 B2 | 4/2011 | Veldman et al. |
| 7,935,134 B2 | 5/2011 | Reglos et al. |
| 7,942,902 B2 | 5/2011 | Schwab |
| 7,959,653 B2 | 6/2011 | Thramann et al. |
| 7,963,978 B2 | 6/2011 | Winslow et al. |
| 7,985,243 B2 | 7/2011 | Winslow et al. |
| 8,012,184 B2 | 9/2011 | Schlapfer et al. |
| 8,016,860 B2 | 9/2011 | Carl et al. |
| 8,021,400 B2 | 9/2011 | Marino et al. |
| 8,029,543 B2 | 10/2011 | Young et al. |
| 8,029,546 B2 | 10/2011 | Capote et al. |
| 8,034,078 B2 | 10/2011 | Laskowitz et al. |
| 8,034,084 B2 | 10/2011 | Landry et al. |
| 8,043,345 B2 | 10/2011 | Carl et al. |
| 8,048,113 B2 | 11/2011 | Winslow et al. |
| 8,052,722 B2 | 11/2011 | Winslow et al. |
| 8,066,743 B2 | 11/2011 | Young et al. |
| 8,070,775 B2 | 12/2011 | Winslow et al. |
| 8,070,776 B2 | 12/2011 | Winslow et al. |
| 8,075,594 B2 | 12/2011 | Purcell |
| 8,097,022 B2 | 1/2012 | Marik |
| 8,114,134 B2 | 2/2012 | Winslow et al. |
| 8,114,158 B2 | 2/2012 | Carl et al. |
| 8,118,837 B2 | 2/2012 | Lemoine |
| 8,147,524 B2 | 4/2012 | Piza Vallespir |

(56) References Cited

U.S. PATENT DOCUMENTS

| | | |
|---|---|---|
| 8,162,979 B2 | 4/2012 | Sachs et al. |
| 8,167,908 B2 | 5/2012 | Ely et al. |
| 8,192,471 B2 | 6/2012 | Ludwig et al. |
| 8,221,466 B2 | 7/2012 | Asaad et al. |
| 8,262,696 B2 | 9/2012 | Falahee |
| 8,292,934 B2 | 10/2012 | Justis et al. |
| 8,323,319 B2 | 12/2012 | Mazda et al. |
| 8,353,934 B2 | 1/2013 | Drewry et al. |
| 8,357,182 B2 | 1/2013 | Seme |
| 8,357,183 B2 | 1/2013 | Seme et al. |
| 8,361,117 B2 | 1/2013 | Michielli et al. |
| 8,403,958 B2 | 3/2013 | Schwab |
| 8,414,614 B2 | 4/2013 | Firkins et al. |
| 8,414,617 B2 | 4/2013 | Young et al. |
| 8,470,001 B2 | 6/2013 | Trautwein et al. |
| RE44,392 E | 7/2013 | Hynes |
| 8,475,499 B2 | 7/2013 | Cournoyer et al. |
| 8,480,712 B1 | 7/2013 | Samuel et al. |
| 8,518,086 B2 | 8/2013 | Seme et al. |
| 2001/0037111 A1 | 11/2001 | Dixon et al. |
| 2002/0032442 A1 | 3/2002 | Altarac et al. |
| 2002/0133155 A1 | 9/2002 | Ferree |
| 2002/0143329 A1 | 10/2002 | Serhan et al. |
| 2002/0151978 A1 | 10/2002 | Zacouto et al. |
| 2002/0169448 A1 | 11/2002 | Vanacker |
| 2003/0040746 A1 | 2/2003 | Mitchell et al. |
| 2003/0045878 A1 | 3/2003 | Petit et al. |
| 2003/0093117 A1 | 5/2003 | Saadat |
| 2003/0109881 A1 | 6/2003 | Shirado et al. |
| 2003/0114853 A1 | 6/2003 | Burgess et al. |
| 2003/0153915 A1 | 8/2003 | Nekozuka et al. |
| 2003/0220643 A1 | 11/2003 | Ferree |
| 2004/0006391 A1 | 1/2004 | Reiley |
| 2004/0049274 A1 | 3/2004 | Reiley |
| 2004/0049277 A1 | 3/2004 | Reiley |
| 2004/0097931 A1 | 5/2004 | Mitchell |
| 2004/0106921 A1 | 6/2004 | Cheung et al. |
| 2004/0149065 A1 | 8/2004 | Moran |
| 2004/0167520 A1 | 8/2004 | Zucherman et al. |
| 2004/0215190 A1 | 10/2004 | Nguyen et al. |
| 2004/0230201 A1 | 11/2004 | Yuan et al. |
| 2004/0230304 A1 | 11/2004 | Yuan et al. |
| 2005/0027361 A1 | 2/2005 | Reiley |
| 2005/0033291 A1 | 2/2005 | Ebara |
| 2005/0033295 A1 | 2/2005 | Wisnewski |
| 2005/0043797 A1 | 2/2005 | Lee |
| 2005/0043799 A1 | 2/2005 | Reiley |
| 2005/0049705 A1 | 3/2005 | Hale et al. |
| 2005/0055096 A1 | 3/2005 | Serhan et al. |
| 2005/0080420 A1 | 4/2005 | Farris et al. |
| 2005/0080486 A1 | 4/2005 | Fallin et al. |
| 2005/0107789 A1 | 5/2005 | Sweeney |
| 2005/0113927 A1 | 5/2005 | Malek |
| 2005/0113928 A1 | 5/2005 | Cragg et al. |
| 2005/0131537 A1 | 6/2005 | Hoy et al. |
| 2005/0131538 A1 | 6/2005 | Chervitz et al. |
| 2005/0149030 A1 | 7/2005 | Serhan et al. |
| 2005/0154390 A1 | 7/2005 | Biedermann et al. |
| 2005/0165396 A1 | 7/2005 | Fortin et al. |
| 2005/0171538 A1 | 8/2005 | Sgier et al. |
| 2005/0177240 A1 | 8/2005 | Blain |
| 2005/0203509 A1 | 9/2005 | Chinnaian et al. |
| 2005/0203511 A1 | 9/2005 | Wilson-MacDonald et al. |
| 2005/0203514 A1 | 9/2005 | Jahng et al. |
| 2005/0203516 A1 | 9/2005 | Biedermann et al. |
| 2005/0209603 A1 | 9/2005 | Zucherman et al. |
| 2005/0216004 A1 | 9/2005 | Schwab |
| 2005/0228326 A1 | 10/2005 | Kalfas et al. |
| 2005/0228377 A1 | 10/2005 | Chao et al. |
| 2005/0234453 A1 | 10/2005 | Shaolian et al. |
| 2005/0240264 A1 | 10/2005 | Tokish et al. |
| 2005/0245929 A1 | 11/2005 | Winslow et al. |
| 2005/0261685 A1 | 11/2005 | Fortin et al. |
| 2005/0261770 A1 | 11/2005 | Kuiper et al. |
| 2005/0267470 A1 | 12/2005 | McBride |
| 2005/0267579 A1 | 12/2005 | Reiley et al. |
| 2006/0004449 A1 | 1/2006 | Goble et al. |
| 2006/0009767 A1 | 1/2006 | Kiester |
| 2006/0009847 A1 | 1/2006 | Reiley |
| 2006/0009849 A1 | 1/2006 | Reiley |
| 2006/0036246 A1 | 2/2006 | Carl et al. |
| 2006/0036256 A1 | 2/2006 | Carl et al. |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0047282 A1 | 3/2006 | Gordon |
| 2006/0058790 A1 | 3/2006 | Carl et al. |
| 2006/0058791 A1 | 3/2006 | Broman et al. |
| 2006/0058792 A1 | 3/2006 | Hynes |
| 2006/0064091 A1 | 3/2006 | Ludwig et al. |
| 2006/0084976 A1 | 4/2006 | Borgstrom et al. |
| 2006/0084996 A1 | 4/2006 | Metz Stavenhagen |
| 2006/0085075 A1 | 4/2006 | McLeer |
| 2006/0116686 A1 | 6/2006 | Crozet |
| 2006/0142758 A1 | 6/2006 | Petit |
| 2006/0142760 A1 | 6/2006 | McDonnell |
| 2006/0149234 A1 | 7/2006 | de Coninck |
| 2006/0189984 A1 | 8/2006 | Fallin et al. |
| 2006/0200149 A1 | 9/2006 | Hoy et al. |
| 2006/0212034 A1 | 9/2006 | Triplett et al. |
| 2006/0217712 A1 | 9/2006 | Mueller et al. |
| 2006/0217715 A1 | 9/2006 | Serhan et al. |
| 2006/0217718 A1 | 9/2006 | Chervitz et al. |
| 2006/0229616 A1 | 10/2006 | Albert et al. |
| 2006/0241594 A1 | 10/2006 | McCarthy et al. |
| 2006/0241598 A1 | 10/2006 | Khalili |
| 2006/0247627 A1 | 11/2006 | Farris |
| 2006/0253118 A1 | 11/2006 | Bailey |
| 2006/0271050 A1 | 11/2006 | Piza Vallespir |
| 2006/0276787 A1 | 12/2006 | Zubok et al. |
| 2006/0293663 A1 | 12/2006 | Walkenhorst et al. |
| 2007/0005062 A1 | 1/2007 | Lange et al. |
| 2007/0016296 A1 | 1/2007 | Triplett et al. |
| 2007/0055373 A1 | 3/2007 | Hudgins et al. |
| 2007/0073293 A1 | 3/2007 | Martz et al. |
| 2007/0079517 A1 | 4/2007 | Augostino et al. |
| 2007/0083200 A1 | 4/2007 | Gittings et al. |
| 2007/0093814 A1 | 4/2007 | Callahan et al. |
| 2007/0093833 A1 | 4/2007 | Kuiper et al. |
| 2007/0161987 A1 | 7/2007 | Capote et al. |
| 2007/0161993 A1 | 7/2007 | Lowery et al. |
| 2007/0161994 A1 | 7/2007 | Lowery et al. |
| 2007/0162002 A1 | 7/2007 | Tornier |
| 2007/0167946 A1* | 7/2007 | Triplett ............ A61B 17/1757 606/279 |
| 2007/0167947 A1 | 7/2007 | Gittings |
| 2007/0168035 A1 | 7/2007 | Koske |
| 2007/0185492 A1 | 8/2007 | Chervitz et al. |
| 2007/0191846 A1 | 8/2007 | Bruneau et al. |
| 2007/0198014 A1 | 8/2007 | Graf et al. |
| 2007/0213716 A1 | 9/2007 | Lenke et al. |
| 2007/0219556 A1 | 9/2007 | Altarac et al. |
| 2007/0225712 A1 | 9/2007 | Altarac et al. |
| 2007/0225713 A1 | 9/2007 | Altarac et al. |
| 2007/0233075 A1 | 10/2007 | Dawson |
| 2007/0233090 A1 | 10/2007 | Naifeh et al. |
| 2007/0233093 A1 | 10/2007 | Falahee |
| 2007/0238335 A1 | 10/2007 | Veldman et al. |
| 2007/0270803 A1 | 11/2007 | Giger et al. |
| 2007/0270805 A1 | 11/2007 | Miller et al. |
| 2007/0270817 A1 | 11/2007 | Rezach |
| 2007/0270836 A1 | 11/2007 | Bruneau et al. |
| 2007/0270837 A1 | 11/2007 | Eckhardt et al. |
| 2007/0270838 A1 | 11/2007 | Bruneau et al. |
| 2007/0270967 A1 | 11/2007 | Fallin et al. |
| 2007/0276374 A1 | 11/2007 | Broman et al. |
| 2007/0288011 A1 | 12/2007 | Logan |
| 2007/0288024 A1 | 12/2007 | Gollogly |
| 2008/0015577 A1 | 1/2008 | Loeb |
| 2008/0021466 A1 | 1/2008 | Shadduck et al. |
| 2008/0021469 A1 | 1/2008 | Holt |
| 2008/0027436 A1 | 1/2008 | Cournoyer et al. |
| 2008/0045954 A1 | 2/2008 | Reiley et al. |
| 2008/0065069 A1 | 3/2008 | Betz et al. |

(56) References Cited

U.S. PATENT DOCUMENTS

| | | |
|---|---|---|
| 2008/0077143 A1 | 3/2008 | Shluzas |
| 2008/0086213 A1 | 4/2008 | Reiley |
| 2008/0091202 A1 | 4/2008 | Reiley |
| 2008/0091210 A1 | 4/2008 | Reiley |
| 2008/0091268 A1 | 4/2008 | Reiley |
| 2008/0097437 A1 | 4/2008 | Reiley |
| 2008/0097438 A1 | 4/2008 | Reiley |
| 2008/0097439 A1 | 4/2008 | Reiley |
| 2008/0097440 A1 | 4/2008 | Reiley et al. |
| 2008/0097441 A1 | 4/2008 | Hayes et al. |
| 2008/0097446 A1 | 4/2008 | Reiley et al. |
| 2008/0097609 A1 | 4/2008 | Reiley |
| 2008/0097612 A1 | 4/2008 | Reiley |
| 2008/0097613 A1 | 4/2008 | Reiley et al. |
| 2008/0132951 A1 | 6/2008 | Reiley et al. |
| 2008/0140202 A1 | 6/2008 | Allard et al. |
| 2008/0167688 A1 | 7/2008 | Fauth et al. |
| 2008/0177326 A1 | 7/2008 | Thompson |
| 2008/0183209 A1 | 7/2008 | Robinson et al. |
| 2008/0183212 A1 | 7/2008 | Veldman et al. |
| 2008/0195100 A1 | 8/2008 | Capote et al. |
| 2008/0195153 A1 | 8/2008 | Thompson |
| 2008/0195154 A1 | 8/2008 | Brown et al. |
| 2008/0200953 A1 | 8/2008 | Reiley et al. |
| 2008/0221622 A1 | 9/2008 | Triplett et al. |
| 2008/0228227 A1 | 9/2008 | Brown et al. |
| 2008/0234737 A1 | 9/2008 | Boschert |
| 2008/0234739 A1 | 9/2008 | Hudgins et al. |
| 2008/0262546 A1 | 10/2008 | Calvosa et al. |
| 2008/0269805 A1 | 10/2008 | Dekutoski et al. |
| 2008/0275507 A1 | 11/2008 | Triplett et al. |
| 2008/0292161 A1 | 11/2008 | Funk et al. |
| 2008/0306535 A1 | 12/2008 | Winslow et al. |
| 2008/0306536 A1 | 12/2008 | Frigg et al. |
| 2008/0319483 A1 | 12/2008 | Triplett et al. |
| 2008/0319484 A1 | 12/2008 | Fauth |
| 2008/0319485 A1 | 12/2008 | Fauth et al. |
| 2008/0319488 A1 | 12/2008 | Helgerson |
| 2008/0319489 A1 | 12/2008 | Triplett |
| 2009/0012565 A1 | 1/2009 | Sachs et al. |
| 2009/0012566 A1 | 1/2009 | Fauth |
| 2009/0018583 A1 | 1/2009 | Song et al. |
| 2009/0024134 A1 | 1/2009 | Triplett et al. |
| 2009/0024135 A1 | 1/2009 | Triplett et al. |
| 2009/0024166 A1 | 1/2009 | Carl et al. |
| 2009/0024167 A1 | 1/2009 | Chervitz et al. |
| 2009/0024168 A1 | 1/2009 | Chervitz et al. |
| 2009/0024169 A1 | 1/2009 | Triplett et al. |
| 2009/0030459 A1 | 1/2009 | Hoy et al. |
| 2009/0030460 A1 | 1/2009 | Chervitz et al. |
| 2009/0030461 A1 | 1/2009 | Hoy et al. |
| 2009/0036929 A1 | 2/2009 | Reglos et al. |
| 2009/0048632 A1 | 2/2009 | Firkins et al. |
| 2009/0062864 A1 | 3/2009 | Ludwig et al. |
| 2009/0062915 A1 | 3/2009 | Kohm et al. |
| 2009/0069849 A1 | 3/2009 | Oh et al. |
| 2009/0082871 A1 | 3/2009 | Fallin et al. |
| 2009/0088802 A1 | 4/2009 | Fallin |
| 2009/0093820 A1 | 4/2009 | Trieu et al. |
| 2009/0099607 A1 | 4/2009 | Fallin et al. |
| 2009/0112207 A1 | 4/2009 | Walker et al. |
| 2009/0112262 A1 | 4/2009 | Pool et al. |
| 2009/0112263 A1 | 4/2009 | Pool et al. |
| 2009/0125062 A1 | 5/2009 | Arnin |
| 2009/0194206 A1 | 8/2009 | Jeon et al. |
| 2009/0204156 A1 | 8/2009 | McClintock et al. |
| 2009/0259256 A1 | 10/2009 | Miller |
| 2009/0281575 A1 | 11/2009 | Carls et al. |
| 2010/0057129 A1 | 3/2010 | Goble et al. |
| 2010/0076493 A1 | 3/2010 | Fauth et al. |
| 2010/0082107 A1 | 4/2010 | Fauth et al. |
| 2010/0087880 A1 | 4/2010 | Fauth et al. |
| 2010/0100130 A1 | 4/2010 | Carl et al. |
| 2010/0100133 A1 | 4/2010 | Carl et al. |
| 2010/0106192 A1 | 4/2010 | Barry |
| 2010/0137913 A1 | 6/2010 | Khatchadourian et al. |
| 2010/0249836 A1 | 9/2010 | Seme |
| 2010/0249837 A1 | 9/2010 | Seme et al. |
| 2010/0256684 A1 | 10/2010 | Seme et al. |
| 2010/0274286 A1 | 10/2010 | Blain et al. |
| 2010/0286730 A1 | 11/2010 | Gordon |
| 2010/0318129 A1 | 12/2010 | Seme et al. |
| 2011/0054536 A1 | 3/2011 | Elsebaie et al. |
| 2011/0060367 A1 | 3/2011 | Stauber |
| 2011/0066188 A1 | 3/2011 | Seme et al. |
| 2011/0245876 A1 | 10/2011 | Brumfield |
| 2012/0109197 A1 | 5/2012 | Carl et al. |
| 2012/0158064 A1* | 6/2012 | Kroll ............... A61B 17/7052 606/250 |
| 2012/0221057 A1 | 8/2012 | Zhang et al. |
| 2013/0123851 A1 | 5/2013 | Seme et al. |
| 2013/0123853 A1 | 5/2013 | Seme et al. |
| 2013/0184757 A1 | 7/2013 | Seme et al. |
| 2013/0211455 A1 | 8/2013 | Seme |
| 2013/0231703 A1 | 9/2013 | Seme et al. |
| 2014/0236234 A1 | 8/2014 | Kroll et al. |

FOREIGN PATENT DOCUMENTS

| | | |
|---|---|---|
| EP | 0418387 A1 | 3/1991 |
| EP | 0260044 B1 | 5/1991 |
| EP | 0322334 B1 | 2/1992 |
| EP | 1281361 A1 | 2/2003 |
| EP | 1600112 A1 | 11/2005 |
| FR | 2697744 A1 | 5/1994 |
| FR | 2736535 A1 | 1/1997 |
| FR | 2781359 A1 | 1/2000 |
| FR | 2801492 A1 | 6/2001 |
| FR | 2872021 A1 | 12/2005 |
| FR | 2900563 A1 | 11/2007 |
| GB | 0780652 A | 8/1957 |
| SU | 0888968 A1 | 12/1981 |
| WO | WO9213496 A1 | 8/1992 |
| WO | WO2004017705 A2 | 3/2004 |
| WO | WO2006010844 A1 | 2/2006 |
| WO | WO2006017641 A2 | 2/2006 |
| WO | WO2006136937 A2 | 12/2006 |
| WO | WO2007051924 A1 | 5/2007 |
| WO | WO2008086467 A2 | 7/2008 |
| WO | WO2008154313 A1 | 12/2008 |
| WO | WO2010053662 A1 | 5/2010 |
| WO | WO2010056650 A1 | 5/2010 |
| WO | WO2010111500 A2 | 9/2010 |
| WO | 2014062942 A1 | 4/2014 |

OTHER PUBLICATIONS

International Search Report and Written Opinion issued in PCT/US2013/065488, mailed Feb. 18, 2014, 10 pages.

Berry, James L et al., A Morphometric Study of Human Lumbar and Selected Thoracic Vertebrae, 12 SPINE 362 (1987).

European Search Report issued in EP Application No. 12154799, completed Mar. 2, 2012, 9 pages.

Fujita, Masaru et al., A Biomechanical Analysis of Sublaminar and Subtransverse Process Fixation Using Metal Wires and Polyethylene Cables, 31 SPINE 2202 (2006).

Girardi, Federico P. et al., Safety of Sublaminar Wires With Isola Instrumentation for the Treatment of Idiopathic Scoliosis, 25 SPINE 691 (2000).

International Application No. PCT/US2008/065979, filed Jun. 5, 2008, entitled Medical Device and Method to Correct Deformity.

International Application No. PCT/US2009/063833, filed Nov. 10, 2009, entitled Growth Directed Vertebral Fixation System With Distractible Connector(s) and Apical Control.

International Application No. PCT/US2010/028684, filed Mar. 25, 2010, entitled Semi-Constrained Anchoring System.

International Search Report and Written Opinion issued in PCT/US2005/027692, mailed May 19, 2008, 4 pages.

International Search Report and Written Opinion issued in PCT/US2008/065979, mailed Oct. 2, 2008, 7 pages.

(56) References Cited

OTHER PUBLICATIONS

International Search Report and Written Opinion issued in PCT/US2009/063833, mailed Mar. 15, 2010, 14 pages.
International Search Report and Written Opinion issued in PCT/US2010/028684, mailed Sep. 28, 2010, 19 pages.
International Search Report and Written Opinion issued in PCT/US2010/036375, mailed Sep. 10, 2010, 16 pages.
International Search Report and Written Opinion issued in PCT/US2010/047117, mailed Dec. 2, 2010.
International Search Report and Written Opinion issued in PCT/US2011/049693, mailed Nov. 15, 2011, 16 pages.
International Search Report and Written Opinion issued in PCT/US2012/065262, mailed Feb. 5, 2013, 8 pages.
Invitation to Pay Additional Fees and Partial Search Report issued in PCT/US2010/028684, mailed Jun. 30, 2010, 6 pages.
Liljenqvist, Ulf R. et al., Analysis of Vertebral Morphology in Idiopathic Scoliosis with Use of Magnetic Resonance Imaging and Multiplanar Reconstruction, 84 J Bone Joint Surg Am. 359 (2002).
Molnar, Szabolcs et al., Ex Vivo and In Vitro Determination of the Axial Rotational Axis of the Human Thoracic Spine, 31 SPINE E984 (2006).
Rajasekaran, S. et al., Eighteen-Level Analysis of Vertebral Rotation Following Harrington-Luque Instrumentation in Idiopathic Scoliosis, 76 J Bone Joint Surg Am. 104 (1994).
Wenger, Dennis R. et al., Biomechanics of Scoliosis Correction by Segmental Spinal Instrumentation, 7 SPINE 260 (1982).
White III, Augustus A. et al., Biomechancis of the Spine 28-29, Tbl. 1-5 (2d ed. 1990).
Extended European Search Report for EP 15 18 0519 dated Jan. 25, 2016.

\* cited by examiner

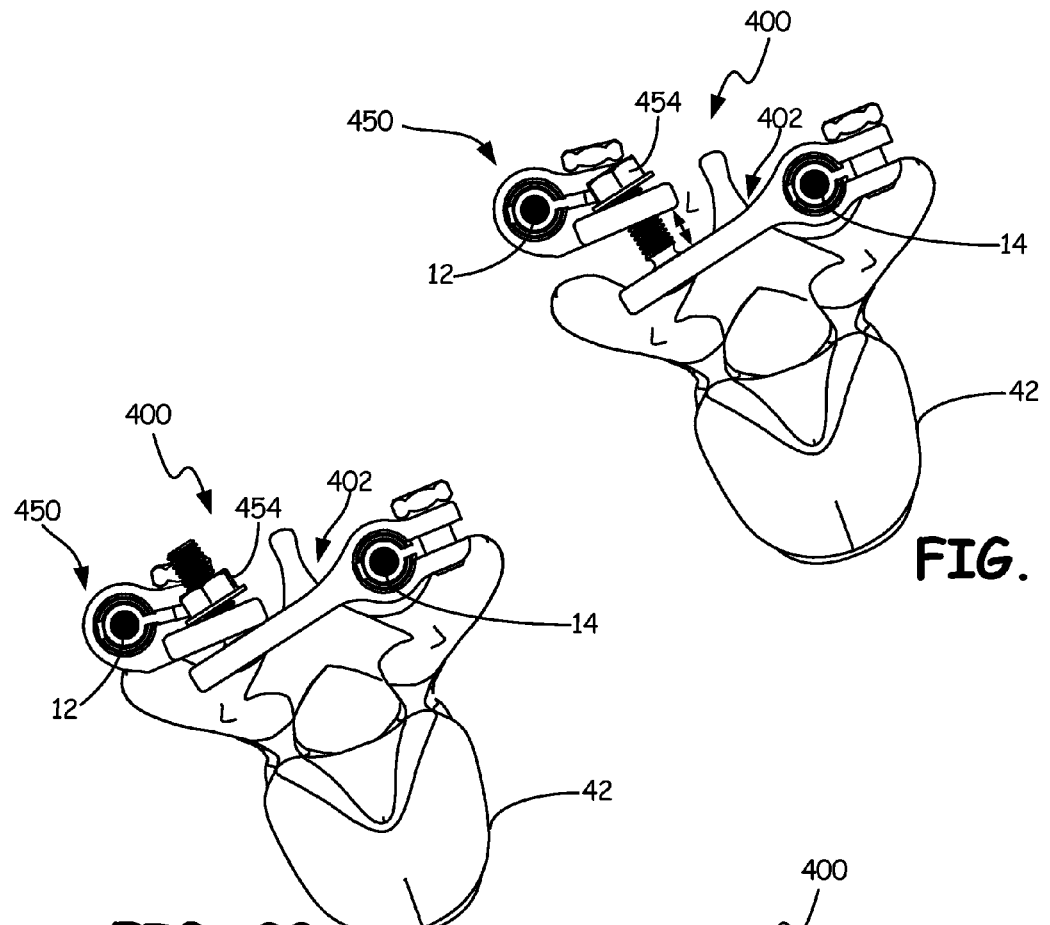
FIG. 27
FIG. 28
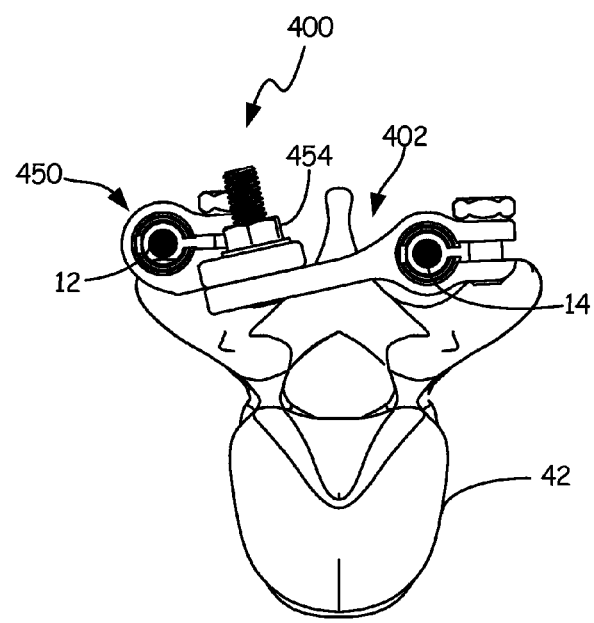
FIG. 29

TRANSVERSE COUPLER ADJUSTER SPINAL CORRECTION SYSTEMS AND METHODS

BACKGROUND

Many systems have been utilized to treat spinal deformities such as scoliosis, spondylolisthesis, and a variety of others. Primary surgical methods for correcting a spinal deformity utilize instrumentation to correct the deformity, as well as implantable hardware systems to rigidly stabilize and maintain the correction.

SUMMARY

Some embodiments relate to systems, devices, and associated methods for correcting spinal column deformities that promote ease of use and surgical technique, help minimize attachment anchor sites, facilitate use of straight or contoured rods, and/or help promote a more natural, physiologic motion of the spinal column as an adjunct to fusion or non-fusion treatment methods.

Some embodiments relate to a transverse coupler for a spinal correction system. The transverse coupler includes an adjustment assembly configured to be secured to a first rod extending longitudinally along a first side of a spine. The adjustment assembly includes a rider, a retainer, and a first rod coupler. The transverse coupler also includes an adjustment arm configured to either partially or fully extend from the first side of the spine to the second side of the spine. The adjustment arm defines a first end, a second end, a first surface, a second surface, and a longitudinal axis extending from the first end to the second end. The transverse coupler also includes a force directing member with an elongate body configured to couple with the rider and the first end of the adjustment arm. The rider and the elongate body are configured to form a complementary fit, wherein the rider can move along the elongate body and couple with the adjustment arm at a plurality of angles.

This summary is not meant to be limiting in nature. While multiple embodiments are disclosed herein, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIGS. 27-29 show the transverse coupler of FIG. 25 at various stages of realignment, according to some embodiments.

Figure 1:
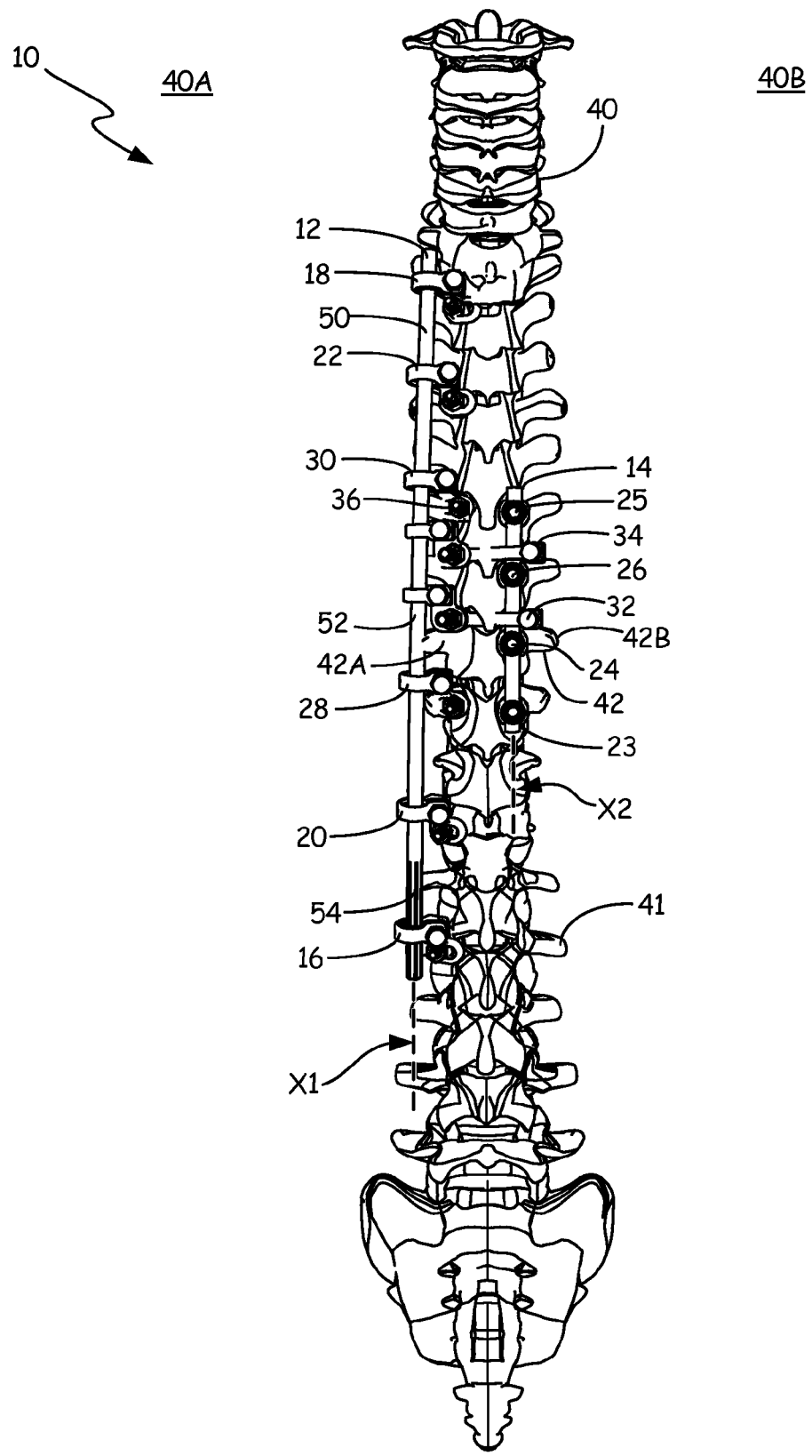
FIG. 1 is a schematic illustration of an implantable spinal correction and fusion system, according to some embodiments.

Various embodiments have been shown by way of example in the drawings and are described in detail below. As stated above, the intention, however, is not to limit the invention by providing such examples.

DETAILED DESCRIPTION

Some embodiments relate to a spinal correction and fusion system for implantation into a patient, as well as associated methods and devices, where the system provides for lateral translational corrective force(s) and/or derotational corrective force(s) on a spinal column with associated instrumentation (e.g., for facilitating vertebral fusion at a selected region of the spine). Some features of the system optionally include implementation of a first, relatively longer rod for correction and stabilization, a second, shorter rod for secondary spinal correction and stabilization. If desired, the stabilization helps promote a fusion. In some embodiments, the spine retains freedom of motion above and below the spinal segment corresponding to the shorter rod, with the first, relatively longer rod remaining implanted. In other embodiments, the first, relatively longer rod is removed following correction and stabilization of the spinal column. A variety of additional or alternative features and advantages of the inventive systems are contemplated and provided by the instant disclosure. As used herein, the phrase "as shown" is indicative of a feature or features shown in the accompanying drawings, although as noted it should be understood that additional or alternative features to those shown are contemplated.

Various planes and associated directions are referenced in the following description, including a sagittal plane defined by two axes, one drawn between a head (superior) and tail (inferior) of the body and one drawn between a back (posterior) and front (anterior) of the body; a coronal plane defined by two axes, one drawn between a center (medial) to side (lateral) of the body and one drawn between a head (superior) and tail (inferior) of the body; and a transverse plane defined by two axes, one drawn between a back and front of the body and one drawing between a center and side of the body. The terms pitch, roll, and yaw are also used, where roll generally refers to angulation, or rotation, in a first plane through which a longitudinal axis of a body orthogonally passes (e.g., rotation about a longitudinal axis corresponding to the spinal column), pitch refers to angulation, or rotation, in a second plane orthogonal to the first plane, and yaw refers to angulation, or rotation, in a third plane orthogonal to the first and second planes. In some embodiments, pitch is angulation in the sagittal plane, yaw is angulation in the coronal plane, and roll is angulation in the transverse plane.

In various embodiments, changes in pitch, yaw, and/or roll occur concurrently or separately as desired. Moreover, as used herein, "lateral translation" is not limited to translation in the medial-lateral direction unless specified as such.

FIG. 1 shows a spinal correction system 10, according to some embodiments. As shown, the system 10 includes a first rod 12, a second rod 14, a plurality of anchors, including a first stabilizing anchor 16, a second stabilizing anchor 18, a third stabilizing anchor 20, a fourth stabilizing anchor 22, a fifth stabilizing anchor 23, a sixth stabilizing anchor 25, a first anchor 24, a second anchor 26, a third anchor 28, a fourth anchor 30, a first transverse coupler 32, a second transverse coupler 34, and a plurality of fasteners 36, such as bone screws or pedicle screws, for securing components of the system 10 to a spine 40 having a first side 40A and a second side 40B.

The system 10 is optionally used to bring the spine 40 to a more natural curvature (e.g., prior to or as a part of a single adjustment or multiple adjustments). In some embodiments, an abnormal curvature in the spinal column 40 has been adjusted to a more natural curvature using other instrumentation, prior to or in conjunction with securing portions of the system 10 to the spinal column 40. In some embodiments, the system 10 is adapted to provide means for leveraged correction, with translation and derotation of the spine 40. If desired, the system 10 is adapted to provide means for selective fusion of the spine 40 following correction. In other embodiments, the system 10 provides means for maintaining a correction to facilitate spinal remodeling in the absence of substantial vertebral fusion (e.g., without permanent vertebral fusion or without any vertebral fusion).

Although the system 10 is shown in FIG. 1 with a selected number of components, such as six stabilizing anchors 16, 18, 20, 22, 23, 25, four anchors 24, 26, 28, 30, two transverse couplers 32, 34, more or fewer components are implemented as appropriate. For example, in some embodiments, the system 10 includes the first rod 12, the second rod 14, a single transverse coupler, such as the first transverse coupler 32, and a first anchor, such as the first anchor 24, with the first rod 12 secured by the first transverse coupler 32 and the second rod 14 secured between the first transverse coupler 32 and the first anchor 24. A variety of other configurations are also contemplated.

As shown in FIG. 1, the first rod 12, also described as an elongate member, is secured to the spinal column 40 at a pre-selected offset from a longitudinal axis of the spinal column 40. For example, the first rod 12 is optionally secured at an offset along a medial-lateral axis ML, or right-left axis, and anterior-posterior axis AP, or back-front axis. In some embodiments, the first rod 12 is secured on the left side of the spinal column 40 as shown. As subsequently described, the offset is optionally selected to cause at least a relative lateral translation (e.g., central or medial movement and/or anterior-posterior movement) and derotational shift (e.g., about a central axis of the spine) of selected vertebrae such that the spinal column 40 exhibits a more natural position.

The first rod 12 is elongate and cylindrical and includes a superior portion 50, an intermediate portion 52, and an inferior portion 54, according to some embodiments. The first rod 12 is adapted, or otherwise structured, as desired, to extend along the spinal column 40. The first rod 12 is optionally contoured to complement a desired spinal curvature. In some embodiments, the first rod 12 is substantially rigid, defining a substantially round cross-section with a mean diameter of about 6 mm and being formed of a suitable biocompatible material, such as titanium alloy ASTM F136, or cobalt chromium alloy ASTM F1537 or any other suitable implantable material. If desired, the first rod 12 incorporates some flex, or springiness while substantially rigidly retaining its shape. Though some material examples have been provided, the first rod 12 is optionally formed of a variety of materials, such as stainless steel or suitable polymeric materials and a variety of cross-sectional shapes.

The first rod 12 has a longitudinal axis X1—where the rod 12 is substantially straight, the longitudinal axis X1 is substantially straight and, where the rod 12 is substantially curved or angled, the longitudinal axis X1 is similarly curved or angled. The sections 50, 52, 54 of the first rod 12 are optionally continuously formed or are formed as separate, connected parts as desired. Expandable rod designs are also contemplated.

As shown in FIG. 1, the second rod 14 is substantially shorter than the first rod 12. For example, the second rod 14 is optionally configured to extend along an apical region of the spine 40 and/or between a desired number of anchors, such as the first and second anchors 24, 26. The second rod 14 is optionally formed of similar materials and with similar cross-section(s) to that of the first rod 12, as desired.

As shown in FIG. 1, the first stabilizing anchor 16 and the first anchor 24 are adapted, or otherwise structured, to be mounted, or fixed to one or more vertebrae, such as vertebrae 41 and 42 located at or near inferior and apical regions, respectively, along the spine 40. Additional examples of stabilizing anchors and anchors in accordance with some embodiments of the system 10 are set forth in U.S. application Ser. No. 13/301,514, filed on Nov. 21, 2011 and entitled TRANSVERSE CONNECTOR FOR SPINAL STABILIZATION SYSTEM, the entire contents of which are hereby incorporated by reference.

Figure 2:
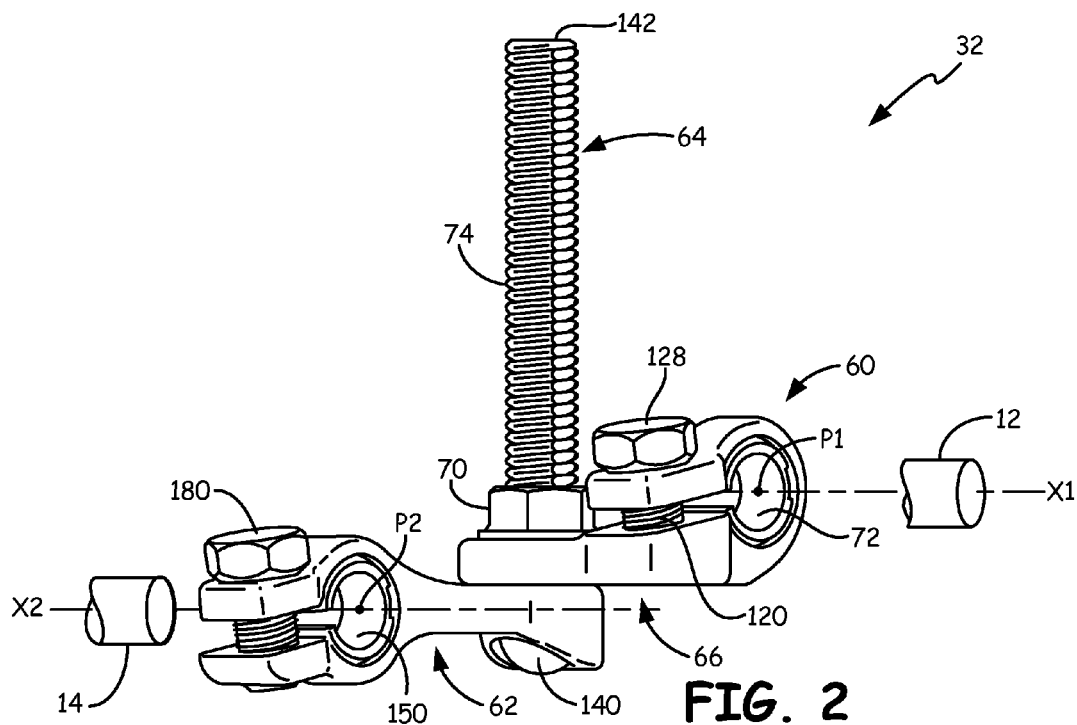
FIG. 2 is an isometric view of a transverse coupler of the system of FIG. 1, according to some embodiments.
Figure 3:
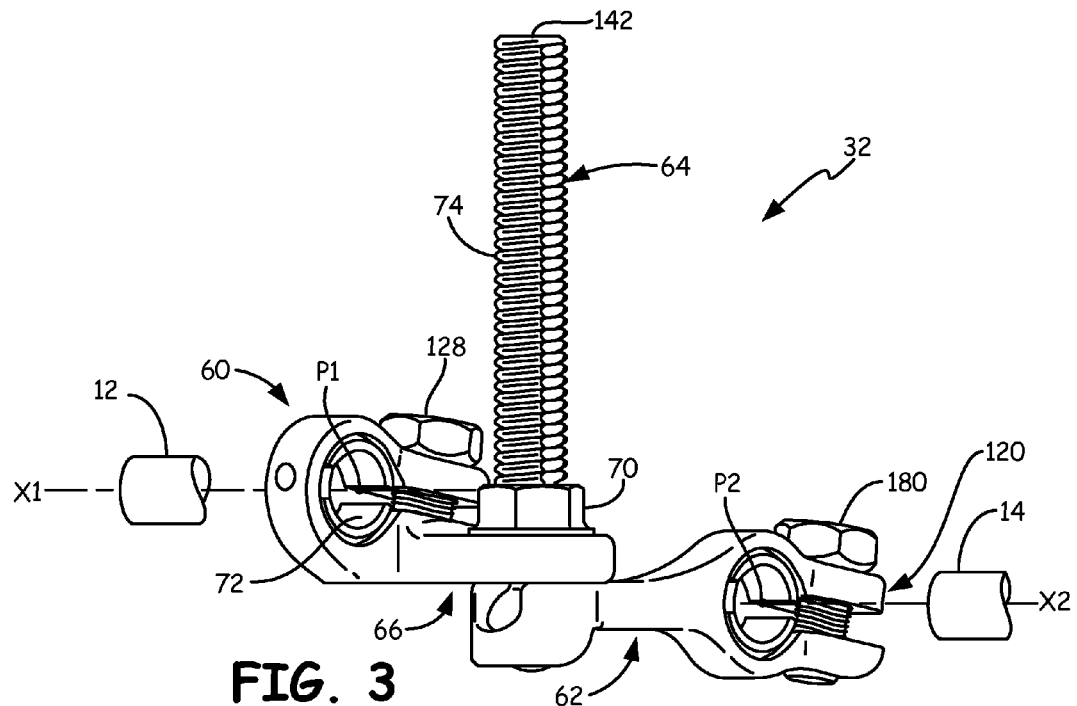
FIG. 3 is an isometric view of the transverse coupler of FIG. 2, according to some embodiments.
Figure 4:
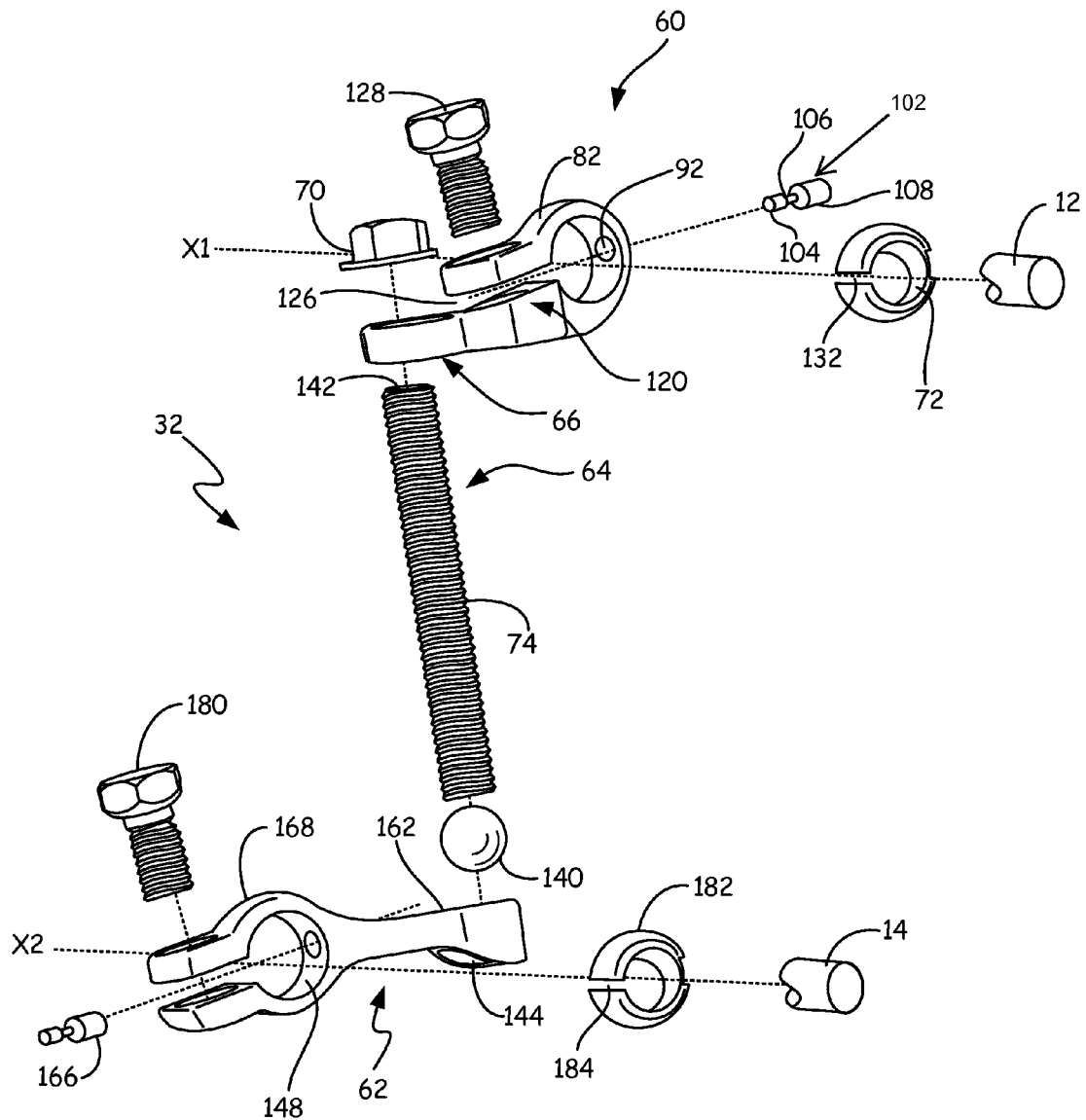
FIG. 4 is an exploded view of the transverse coupler of FIG. 2, according to some embodiments.

FIGS. 2 to 4 show the first transverse coupler 32 (also described as an anchor or connector) of the system 10, according to some embodiments. As shown in FIG. 2, the first transverse coupler 32 is adapted, or otherwise structured, to be positioned laterally across a vertebra, such as the first apical vertebra 42 (FIG. 1) located at or near the apex of the defective curvature along the spine 40. As shown, the first transverse coupler 32 is designed to extend, either partially or fully, from the first side 40A of the spine 40 to the second side 40B of the spine 40.

FIGS. 2 and 3 provide isometric views of the first transverse coupler 32, according to some embodiments. As shown, the first transverse coupler 32 is adapted, or otherwise structured, to receive the first rod 12, such that the first rod 12 is secured laterally relative to a portion of the first transverse coupler 32. In some embodiments, the first rod 12 is substantially prevented from translating in a direction generally perpendicular to the longitudinal axis X1 at a first pivot point P1 while the rod 12 is able to slide axially, or translate axially, along the longitudinal axis X1 through the first pivot point P1 and also to change in pitch and yaw about the first pivot point P1.

In some embodiments, the first transverse coupler 32 is adapted, or otherwise structured, to substantially limit rotation, or roll, of the first rod 12 about the longitudinal axis X1 of the first rod 12. According to some embodiments, the first transverse coupler 32 provides a means for allowing the rod 12 to angulate without substantial lateral translation relative to the portion of the first transverse coupler 32 and without substantial rotation about the longitudinal axis X1.

In some embodiments, the first transverse coupler 32 provides a means for selectively locking the first rod 12 to substantially prevent changes in axial translation, pitch, yaw, and/or roll. The selective locking feature is optionally suitable for constraining movement of the rod 12 under conditions associated with implantation of the system 10 and/or under conditions associated with spinal loading of the system 10 following implantation and securement of the system to the spine 40.

The first transverse coupler 32 is optionally adapted secured to an anchor point on the second side of the spine. In some embodiments, the transverse coupler 32 is secured to an anchor point on the second side 40B of the spine 40 where the anchor point is a spinal anchor directly secured to a vertebral body (not shown). For example, the spinal anchor is optionally a pedicle screw, hook or clamp. In some embodiments, the transverse coupler 32 is secured to an anchor point on the second side 40B of the spine 40 where the anchor point includes a rod coupler configured to be secured to a second rod 14 extending longitudinally along a second side 40B of a spine 40.

In some embodiments, the first transverse coupler 32 is adapted to receive the second rod 14 such that the second rod 14 is secured laterally against lateral translation relative to a portion of the first transverse coupler 32. In some embodiments, the second rod 14 is substantially prevented from translating in a direction substantially perpendicular to the longitudinal axis X2 at a second pivot point P2. In turn, in some embodiments, the second rod 14 is able to slide axially, or translate axially, along a second longitudinal axis X2, relative to the first transverse coupler 32 through a second pivot point P2. The second rod 14 is optionally able to change in pitch and yaw about the second pivot point P2.

The first transverse coupler 32 is optionally adapted, or otherwise structured, to substantially limit rotation, or roll, of the second rod 14 about the second longitudinal axis X2 of the second rod 14. The first transverse coupler 32 provides means for allowing the second rod 14 to angulate without substantial lateral translation relative to the portion of the first transverse coupler 32 and without substantial rotation about the second longitudinal axis X2, according to some embodiments.

In some embodiments, the first transverse coupler 32 provides a means for selectively locking the second rod 14 to substantially prevent changes in axial translation, pitch, yaw, and/or roll. The selective locking feature is optionally suitable for constraining movement of the rod 14 under conditions associated with implantation of the system 10 and/or under conditions associated with spinal loading of the system 10 following implantation and securement of the system to the spine 40.

The first transverse coupler 32 is optionally formed of suitable biocompatible metallic materials, such as titanium, titanium alloy ASTM F136, stainless steel, cobalt chromium alloy ASTM F1537, and/or suitable biocompatible polymeric materials, such as PEEK and/or composite materials.

FIG. 4 is an exploded view of the first transverse coupler 32. As shown, the first transverse coupler 32 includes an adjustment assembly 60 (also described as an adapter or adjustor) adapted to be secured to a first rod 12 extending longitudinally along a first side 40A of the spine 40. According to some embodiments, the adjustment assembly 60 includes a rider 66, an adjustment retainer 70, and a first rod coupler 72 to receive the first rod 12. As shown, the first transverse coupler 32 also includes an adjustment arm 62 adapted to be secured to the second rod 14 and extends from the first side 40A of the spine 40 to a second side 40B of the spine 40, as well as a force directing member 64 having an elongate body 74 adapted to extend between the adjustment assembly 60 and the adjustment arm 62.

Figure 25:
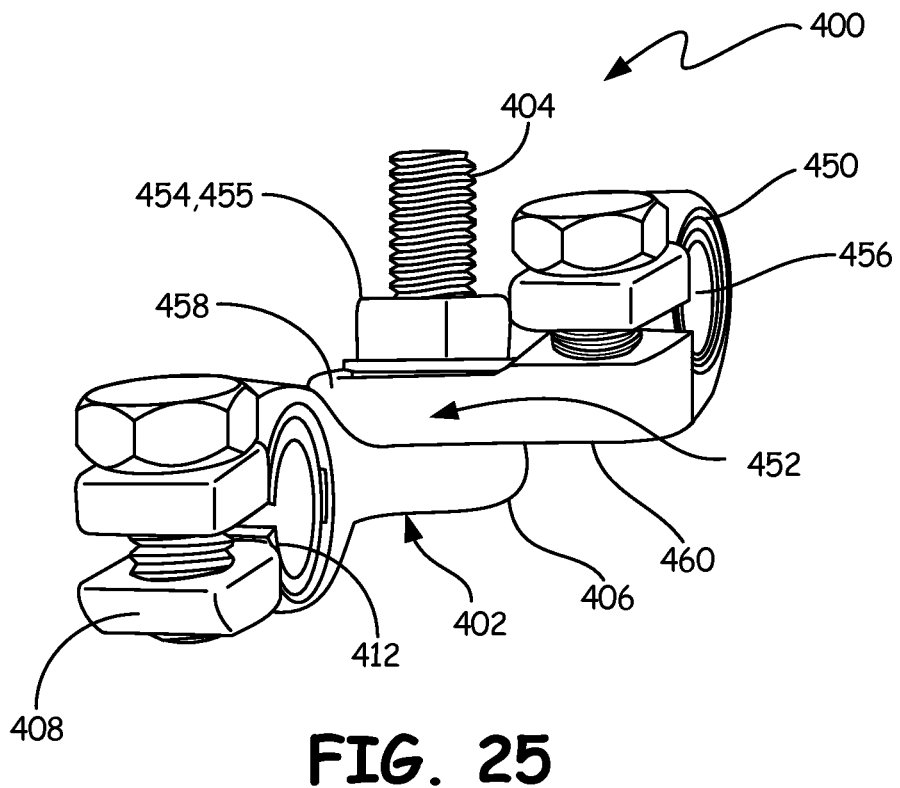
FIG. 25 is an isometric view of an alternative embodiment of a transverse coupler of the system of FIG. 1, according to some embodiments.
Figure 26:
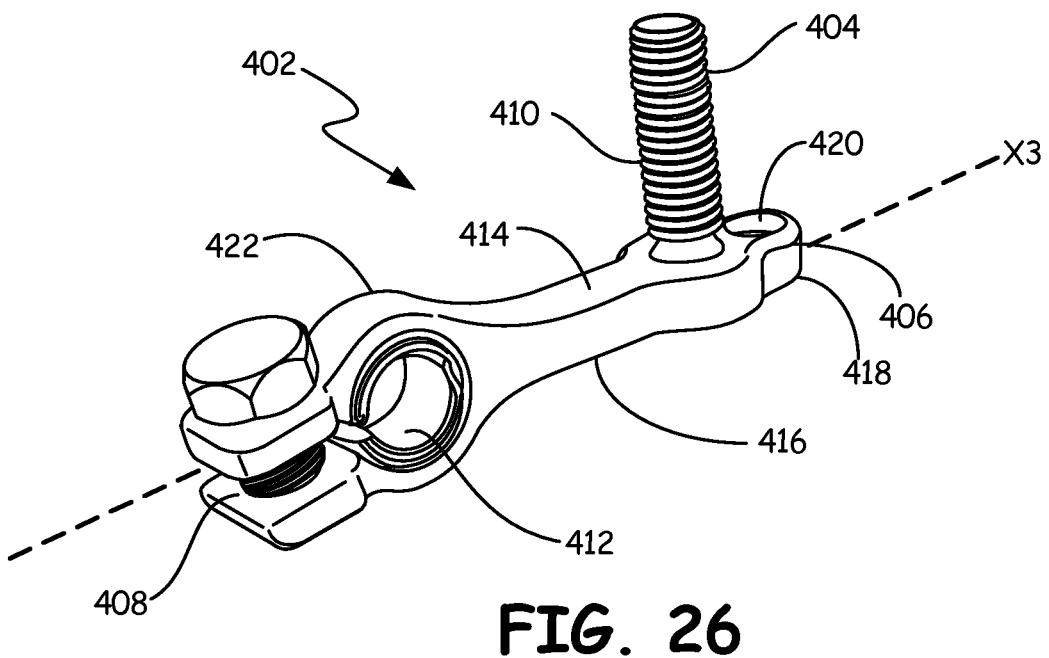
FIG. 26 is a perspective view of the transverse coupler of FIG. 25 with some features not shown to facilitate understanding, according to some embodiments.

As subsequently described, in some embodiments, the first rod coupler 72 is a multi-piece design (e.g. as shown in FIGS. 2-8). In other embodiments, the first rod coupler 72 is a single-piece design adapted, or otherwise structured, for receiving the first rod 12 (FIGS. 25-26).

As shown in FIG. 4, the adjustment assembly 60 connects to the force directing member 64 and the first rod 12, which extends along the first side 40A of the spine 40. As shown in FIG. 1 and FIGS. 13-16, the adjustment assembly 60 and force directing member 64 are optionally adapted to be positioned on the first side 40A of the spine 40. In some embodiments, the adjustment arm 62 is adapted to span across a portion of the first apical vertebra 42 (e.g., lamina-to-lamina or pedicle-to-pedicle on a single vertebra).

FIGS. 5-8 show features of the adjustment assembly 60. As shown, the adjustment assembly 60 has a first rod coupler 72, a rider 66 (also described as a slider or adjuster), and an adjustment retainer 70, also described as a fastener or tightener (see FIGS. 7 and 8).

Figure 5:
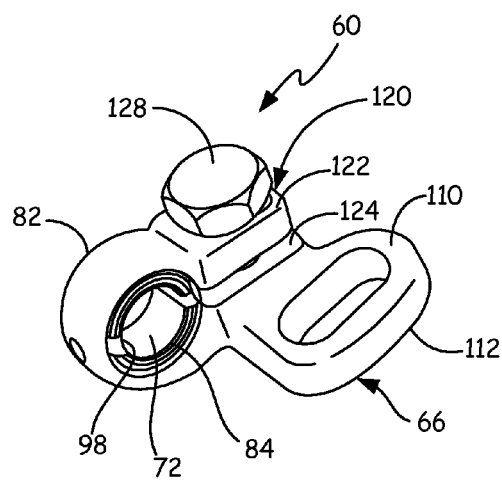
FIG. 5 is a perspective view of a rider of the transverse coupler of FIG. 2, according to some embodiments.
Figure 6:
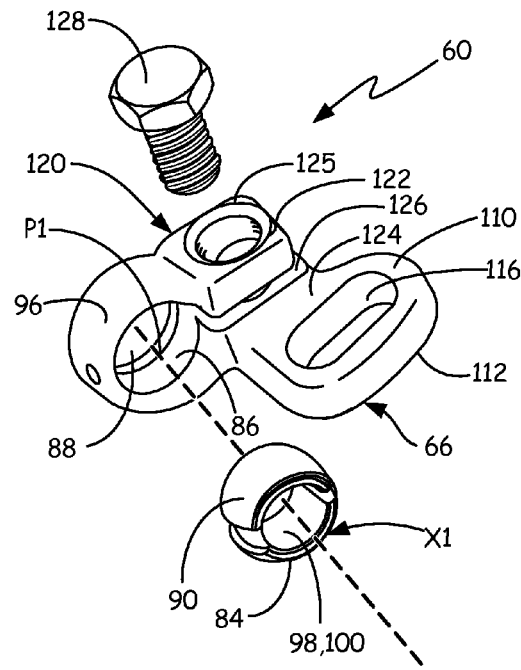
FIG. 6 is an exploded view of the rider of FIG. 5, according to some embodiments.

As shown in FIGS. 4-6, the first rod coupler 72 of the adjustment assembly 60 includes a body 82 and a sleeve insert 84. In some embodiments, the body 82 defines a sleeve aperture 88 extending through a first side 93 of the body 82 to a second side 94 of the body 82. The sleeve aperture 88 is configured for receiving the sleeve insert 84, according to some embodiments. In some embodiments, the sleeve aperture 88 is adapted to mate with the sleeve insert 84, the sleeve insert 84 forming a revolute, substantially concave articulation surface 86. In some embodiments, the sleeve insert 84 forms a revolute, substantially convex articulation surface 90 that complements the sleeve aperture 88. The body 82 has also optionally has a pin chase 92 (e.g. a cylindrical through hole) that extends from the outer surface 96 of the body 82 to the articulation surface 86.

Figure 7:
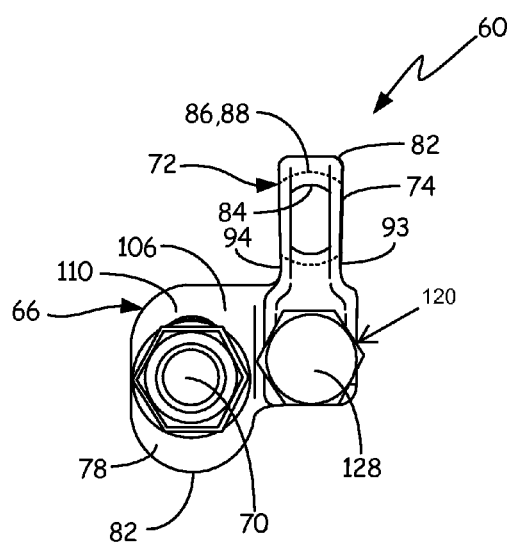
FIG. 7 is a top view of the rider of FIG. 5, according to some embodiments.

FIG. 7 is a top plan view of the adjustment assembly 60 showing some of the internal features of the body 82. As shown, the concave articulation surface 86 of the aperture 88 is adapted, or otherwise structured, to form a substantially complementary fit with the sleeve insert 84. In some embodiments, the sleeve insert 84 is able to be captured by the body 82 within the aperture 88 and have relative angular movement with respect to the body 82.

In some embodiments, the sleeve insert 84 has a passage 98 defining a pivot point P1 through which a portion of the first rod 12 is able to be received. As shown, the pivot point P1 is defined in the passage, where, upon assembly, the first rod 12 passes through the first pivot point P1 such that the longitudinal axis X1 of the rod 12 at the first pivot point P1 is generally concentric with the center of the passage.

As shown, the sleeve insert 84 has a smooth bore 100 for receiving the first rod 12. In some embodiments, the sleeve insert 84 is adapted to help allow the first rod 12 to pass through the passage 98 at the first pivot point P1, where the passage 98 helps allow the rod 12 to angulate about the longitudinal axis X1 at the first pivot point P1 (shown in FIGS. 2, 3, 6, and 8) while rotation and lateral translation of the first rod 12 with respect to the first rod coupler 72 is substantially limited in all planes. In alternative terms, the first rod coupler 72 of the adjustment assembly 60 is configured to be substantially laterally constrained by a first rod 12 when the first rod coupler 72 receives the first rod 12. The first rod coupler 72 selectively locks rotation of the first rod 12 while helping to allow the first rod 12 to axially translate through the first rod coupler 72 and to pivot in pitch and yaw at the first pivot point P1, according to some embodiments.

Figure 8:
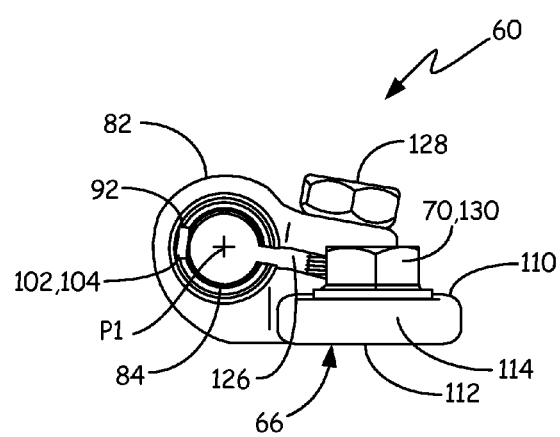
FIG. 8 is a side view of the rider of FIG. 5, according to some embodiments.

As shown in FIGS. 4, 6, and 8, in some embodiments, the body 82 also includes a first protrusion 102 (e.g., a pin) or protrusions (not shown) that extend inwardly into the aperture 88 from the articulation surface 86. The first protrusion 102 is optionally a pin with a head 104, a neck 106, and a body 108, the neck 106 being located between the head 104 and the body 108 (see FIG. 4). The head 104, the neck 106, and the body 108 are optionally substantially cylindrical with the head 104 having a greater diameter than the body 108 and the body 108 having a greater diameter than the neck 106. The first protrusion 102 is optionally received in the pin chase 92 such that the head 104 projects into the aperture 88. In some embodiments the first protrusion 102 and/or body 108 is press fit into the pin chase 92 and/or welded, adhered, or otherwise secured within the pin chase 92. In some embodiments, the first protrusion is temporary and is removable in association with an implantation procedure, providing temporary prevention of roll of the sleeve insert 84 within the body 82 before, during, and/or after securing the system 10 to the spine 40, for example.

As shown, the body of the first rod coupler 72 also includes a locking portion 120. In some embodiments, the locking portion 120 has an upper portion 122 and a lower portion 124 separated by a gap 126 (FIG. 6). In some embodiments, the upper portion 122 has a through slot 125 (FIG. 6) that helps allow a locking member 128 (e.g., a male threaded bolt) to slidably pass through the upper portion 122. The lower portion 124 optionally has a bore (e.g., a female threaded bore), at least partially extending through the lower portion 124. The upper portion 122 and the lower portion 124 can optionally be locked, or clamped, together with the locking member 128 secured across the gap 126. In some embodiments, the locking portion 120 of the first rod coupler 72 is adapted to lock the sleeve insert 84 within the body 82 of the first rod coupler 72.

In some embodiments, the locking portion 120 is adapted to lock the first rod 12 to the first rod coupler 72. As shown in FIG. 4, the sleeve insert 84 has a gap 132 that facilitates locking of the sleeve insert 84 onto the first rod 12. For example, in some implementations, upon sufficiently tightening the locking member 128, the sleeve insert 84 is locked onto rod 12 to arrest axial translation of the rod 12 through the sleeve insert 84. In some implementations, the locking action of the body 82 on the sleeve insert 84 arrests changes in pitch and yaw. In different terms, the rod 12 is able to be selectively locked relative to the first transverse coupler 32 to substantially prevent changes in axial translation, pitch, yaw, and/or roll as desired.

The first rod coupler 72 defines a rod pivot point P1 and is optionally configured to be transitioned from an unlocked state in which a first rod 12 received by the first rod coupler 72 is able to axially translate and change in pitch and yaw about the first rod pivot point P1 to a locked state in which the first rod 12 received by the first rod coupler 72 is locked against axial translation and changes in pitch and yaw about the rod pivot point. When the first rod coupler 72 receives the first rod 12, the first rod coupler 72 is substantially laterally constrained by the first rod, according to some embodiments.

As shown in FIGS. 5-8, the rider 66 (also described as slider or adjuster) includes a first surface 110 and a second surface 112 connected by a lateral wall 114. In some embodiments, the rider 66 is substantially oval-shaped and extends from the lower portion 124 of the locking portion 120. As shown, the first surface 110 of the rider 66 faces generally away from the adjustment arm 62. During operation, the adjustment retainer 70 abuts the first surface 110 of the rider 66 and moves the rider 66 along the force directing member 64, according to some embodiments. Although the adjustment retainer 70 is shown on the rider 66, it should be understood that the adjustment retainer 70 and the rider 66 are not a single unit, but are separate, relatively moveable components, according to some embodiments. As shown, the second surface 112 of the rider 66 faces generally toward the adjustment arm 62. During operation, the second surface 112 of the rider 66 engages with the adjustment arm 62 when the adjustment assembly 60 is moved along the force directing member 64 and brought in contact with the adjustment arm 62, according to some embodiments.

As shown in FIG. 6, the rider 66 also includes a slot 116 extending through the rider 66 from the first surface 110 to the second surface 112. As shown, the slot 116, also described as an articulation aperture, has an elongate transverse cross-section. In some embodiments, the slot 116 is configured to receive the elongate body 74 of the force directing member 64 such that the elongate body 74 of the force directing member 64 is adjustable within the slot 116 in the direction in which the slot 116 is elongated. In operation, the rider 66 is optionally moveable along the force directing member 64 by, for example, moving the rider along the force directing member. The slot 116 is optionally configured to help allow the force directing member 64 extend through the rider 66 at a substantially orthogonal angle relative to the second surface of the rider 66, as well as a variety of additional angles as desired. For example, the slot 116 is optionally configured to help allow the force directing member 64 to angulate, or pivot, within the slot 116 such that the force directing member extends through a plurality of angles (e.g., orthogonal and non-orthogonal) relative to the second surface 112 of the rider 66. In some embodiments, the slot 116 is configured to allow the force directing member 64, but not the adjustment retainer 70 to extend through the slot 116 of the rider 66. Consequently, the adjustment retainer 70 abuts the first surface 110 of the rider 66 adjacent the slot 116 and does not extend through the slot 116 of the rider 66, according to some embodiments.

As shown in FIGS. 7 and 8, the adjustment retainer 70 is configured to couple to the force directing member 64. The adjustment retainer 70 is configured to travel along the force directing member 64 in a direction of a central axis defined by the elongate body 74 of the force directing member 64 as desired. In some embodiments, the adjustment retainer 70 is a threaded cap 130 (e.g., a female threaded nut) configured to mate with and be screwed down the length of the force directing member 64, pressing against the rider 66, and thereby helping to move the rider 66 along the force directing member 64 as the adjustment retainer 70 is actuated along the force directing member 64.

FIGS. 2-4 show features of the force directing member 64 (also described as a connector), according to some embodiments. In some embodiments, the force directing member 64 includes the elongate body 74 and extends from a first end 140 and a second end 142. In other embodiments, the elongate body includes a head portion with a pocket configured to receive a rod, for example, a rod-shaped portion of the rider and/or adjustment arm (not shown). In some embodiments, the force directing member 64 includes a threaded, elongate body 74 adapted to mate with the threaded cap 130 of the adjustment retainer 70. Alternatively, in some embodiments, the elongate body 74 has teeth, barbs or stepped features along the elongate body 74 adapted to mate with teeth, barbs, or complementary features of the adjustment retainer 70. Some examples of the force directing member 64 optionally include, but are not limited to, a threaded screw, a standard bolt, a toggle bolt, a female threaded partial tube, a cable tie, a zip tie, a peg fastener or other type of selectively adjustable mechanism.

The first end 140 of the force directing member 64 is optionally adapted to be received within an aperture 144, also described as an articulation aperture or a socket, of the adjustment arm 62. In some embodiments, the first end 140 of the force directing member 64 is adapted to allow the force directing member 64 to change in pitch, yaw and roll from within the aperture 144. As shown in FIG. 2, the first end 140 is generally spherically shaped and is adapted to fit within the aperture 144. In some embodiments, the first end 140 of the force directing member 64 is adapted to substantially limit the force directing member 64 from substantially changing in pitch, yaw and roll from within the aperture 144. The first end 140 of the force directing member 64 is optionally a generally polygon-shaped end. For example, a force directing member 64 with a square-end, when fit into a complementary polygon-shaped aperture of the adjustment arm 62, is substantially prevented from changing in pitch, yaw, and roll from within the aperture. Alternatively, a force directing member can optionally include a cylinder-end, e.g. a T-shaped first end, which when fit into a complementary shaped aperture of the adjustment arm 62, is substantially prevented from changing in pitch, but allows changes in yaw and roll from within the aperture.

The force directing member 64 is adapted to be secured to the adjustment assembly 60 and the adjustment arm 62 such that the elongate body 74 of the force directing member 64 extends between the rider 66 of the adjustment assembly 60 and the adjustment arm 62, according to some embodiments. The first force directing member 64 has the elongate body 74 optionally defining an effective length L (FIGS. 13 and 14) between the rider 66 of the adjustment assembly 60 and the adjustment arm 62. Alternatively, the elongate body 74 may optionally define the effective length L as the distance between a second surface 112 of the rider 66 and the first end 140 of the force directing member 64 (not shown). The effective length L is dependent on the position of the adjustment retainer 70 along the force directing member 64, according to some embodiments. An effective angle α (FIGS. 17 and 19) between the force directing member 64 and a first surface 160 (shown in FIG. 9) of the adjustment arm 62 is optionally dependent on the position of the first and second rods 12, 14. As the adjustment retainer 70 is engaged, or rotated clockwise (for right hand threaded components), along the force directing member 64, the effective length L is shortened and the angle α is increased as desired (for example, see α1 in FIG. 17). If the adjustment retainer 70 is disengaged, or rotated counter-clockwise (for right hand threaded components), the effective length L is lengthened and the angle α is decreased as desired (for example, see α2 in FIG. 19). Although a screw, or threaded, adjustment mechanism is shown, a variety of alternative adjustment mechanisms (e.g., a pawl and ratchet system) are contemplated.

FIGS. 9-12 show features of the adjustment arm 62 (also described as a transverse connector or arm), according to some embodiments. The adjustment arm 62 is optionally configured to extend from a first side 40A of the spine 40 to a second side 40B of the spine 40. As shown, the adjustment arm 62 includes a second rod coupler 150, a connecting portion 152, and a base portion 154, the adjustment arm having a first end 156, a second end 158, the first surface 160, a second surface 162, and a longitudinal axis X3 extending from the first end 156 to the second end 158.

As shown, the connecting portion 152 of the adjustment arm 62 has an elongate body 164 that extends from the base portion 154 to the second rod coupler 150. In some embodiments, the first surface 160 of the adjustment arm 62 faces generally toward the adjustment assembly 60 and the second surface 162 of the adjustment arm 62 faces generally away the adjustment assembly 60. In operation, the first surface 160 of the adjustment arm 62 also engages with the adjustment assembly 60 when the adjustment assembly 60 is moved along the force directing member 64 and brought in contact with the adjustment arm 62, according to some embodiments.

Figure 9:
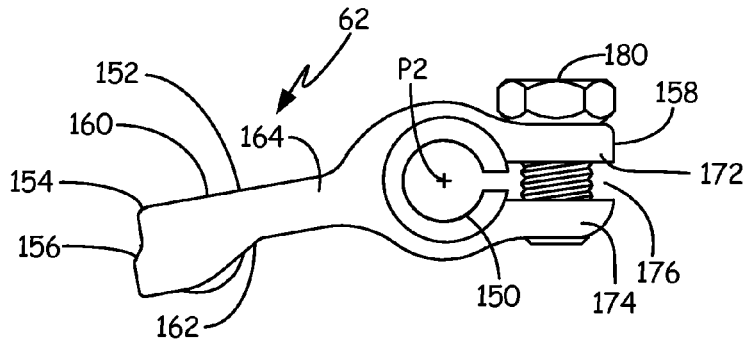
FIG. 9 is a side view of an adjustment arm of the transverse coupler of FIG. 2, according to some embodiments.

FIG. 9 is a side view of the adjustment arm 62, according to some embodiments. As shown, the second end 158 of the adjustment arm 62 includes the second rod coupler 150, which is configured to be secured to a second rod 14 extending longitudinally along a second side 40B of a spine 40. In some embodiments, the second rod coupler 150 of the adjustment arm 62 is substantially similar to the first rod coupler 72 of the adjustment assembly 60, with the exception that the second rod coupler 150 receives the second rod 14. The second rod coupler 150 of the adjustment arm 62 is optionally configured to substantially limit roll of the second rod 14 where the second rod 14 is received by the second rod coupler 150. As shown in FIG. 9, the second rod coupler 150 is adapted to be substantially laterally constrained by the second rod 14 with the second rod 14 being able to axially translate through the second rod coupler 150 and to pivot in pitch and yaw at the second rod coupler 150 at a second pivot point P2.

As shown in FIG. 4, a body 168 of the second rod coupler 150 also includes a second protrusion 166 (e.g., a pin) or protrusions (not shown) that extends inwardly into the aperture from the articulation surface 148. In some embodiments, the second protrusion 166 is substantially similar to the first protrusion 102 of the first rod coupler 72, discussed previously herein, and substantially prevents a sleeve insert 182 from rolling within the body 168 of the second rod coupler 150.

As shown in FIG. 9, the second rod coupler 150 of the adjustment arm 62 includes a locking mechanism similar to the first rod coupler 72. In some embodiments, the locking portion 170 has a first portion 172 and a second portion 174 separated by a gap 176. The first portion 172 and the second portion 174 can be locked, or clamped, together with the locking member 180 is secured into a through slot 178 and across the gap 176, according to some embodiments. As shown, the sleeve insert 182 also has a gap 184 (FIG. 4) that facilitates locking of the sleeve insert 182 onto the second rod 14. For example, upon sufficiently tightening the locking member 180, the sleeve insert 182 is optionally locked onto rod 14 to substantially arrest axial translation of the second rod 14 through the sleeve insert 182. In some embodiments, the locking action of the body 168 of the second rod coupler 150 on the sleeve insert 182 substantially arrests changes in pitch and yaw. In different terms, the second rod 14 is able to be selectively locked relative to the first transverse coupler 32, in accordance with some embodiments. The selective locking feature is optionally suitable for constraining movement of the rod 14 under conditions associated with implantation of the system 10 and/or under conditions associated with spinal loading of the system 10 following implantation and securement of the system to the spine 40.

Figure 10:
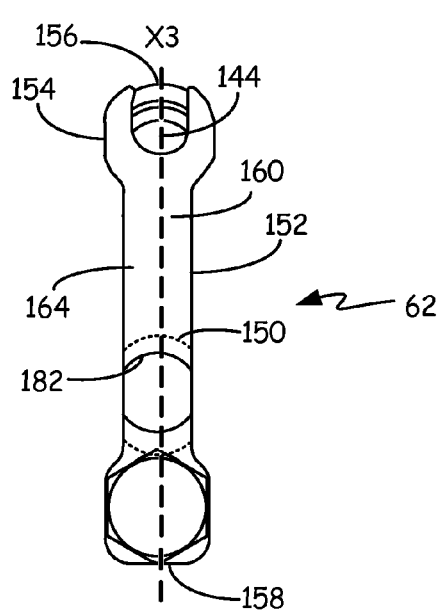
FIG. 10 is a top view of the adjustment arm of FIG. 9, according to some embodiments.
Figure 11:
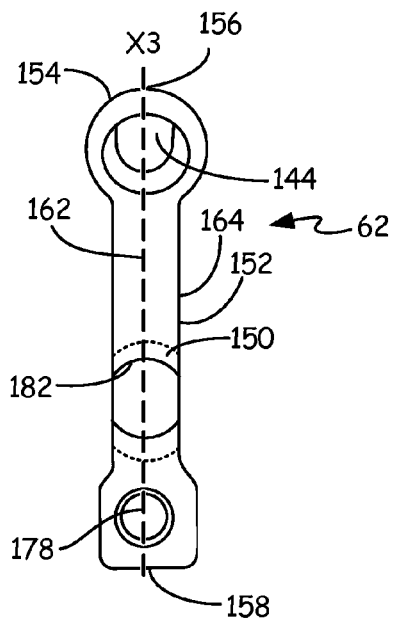
FIG. 11 is a bottom view of the adjustment arm of FIG. 9, according to some embodiments.
Figure 12:
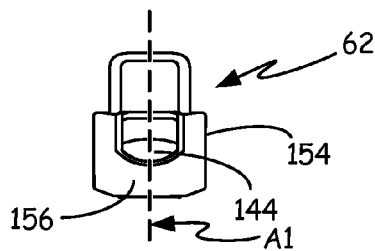
FIG. 12 is a rear view of the adjustment arm of FIG. 9, according to some embodiments.
Figure 13:
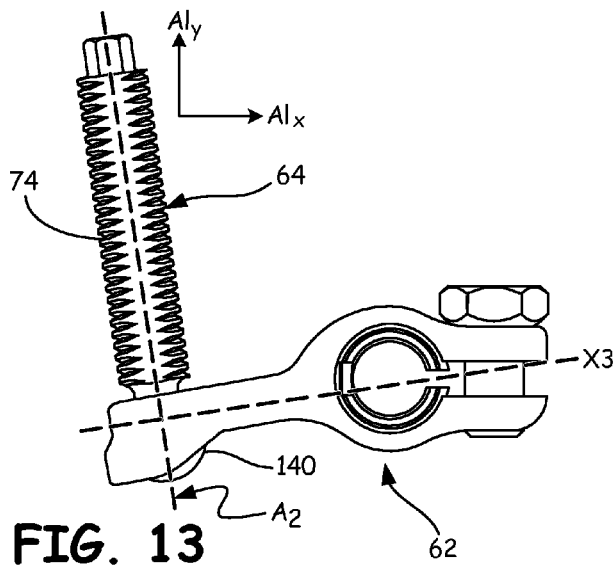
FIGS. 13-16 are side and rear views of a force directing member of the transverse coupler of FIG. 2 and the adjustment arm of FIG. 9 at various angulations, according to some embodiments.

As mentioned previously and as shown in FIGS. 10 and 11, the first end 156 of the adjustment arm 62 includes an articulation aperture 144 extending from the first surface 160 to the second surface 162. In some embodiments, the articulation aperture 144 is adapted to receive the force directing member. The articulate aperture 144 has a revolute, substantially concave inner surface with an elongate opening extending in the direction of the longitudinal axis X3 (FIGS. 10-12).

As shown in FIGS. 13-16, the elongate body 74 of the force directing member 64 extends from the first surface 160 of the adjustment arm 62 at an angle relative to the longitudinal axis X3. In some embodiments, the force directing member 64 extends from first surface 160 of the adjustment arm 62 at an adjustable angle relative to the longitudinal axis X3. The angle may be, for example, optionally adjusted to any angle between 0 to 90 degrees. In some embodiments, the force directing member 64 is rigidly secured to the first end 156 of the adjustment arm 62 and extends from the first surface 160 of the adjustment arm 62 at a substantially fixed angle relative to the longitudinal axis. In some embodiments, the elongate body 74 of the force directing member 64 extends from the first surface 160 of the adjustment arm 62 at a substantially orthogonal angle relative to the longitudinal axis X3.

Figure 14:
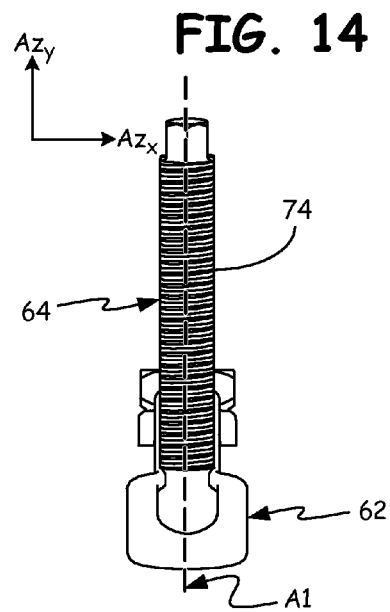
Figure 15:
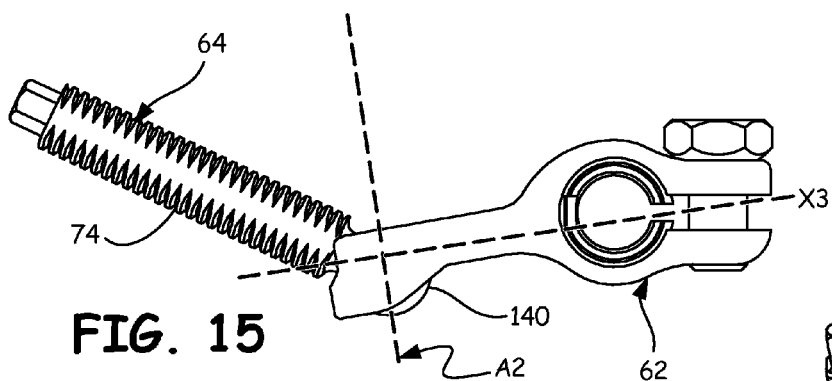
Figure 16:
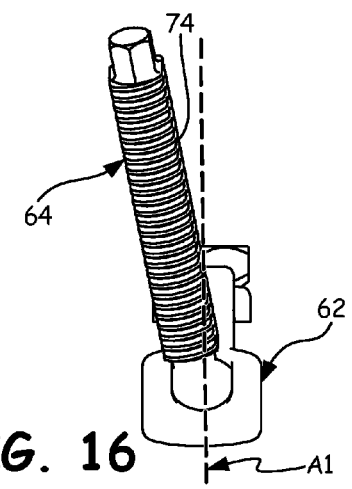

In some embodiments, the spherically shaped first end 140 of the force directing member 64 fits within an articulation aperture 144. The first end 140 of the force directing member 64 is optionally received within the articulation aperture 144 (FIGS. 10 and 11) of the adjustment arm 62 such that the force directing member 64 is able to angulate. In some embodiments, the force directing member 64 is substantially free to angulate in a first plane of angulation A1 (FIGS. 13 and 15) to a greater degree than in other planes of angulation (e.g., a second plane of angulation A2 as shown in FIGS. 14 and 16). The first plane of angulation A1 is depicted as a line (FIGS. 14 and 16). The first plane A1 is defined by the longitudinal axis X3 and the normal axis X4 of the transverse coupler, both falling within the first plane A1. The first plane A1 is generally orthogonal to the second plane A2 while being generally parallel to the longitudinal axis X3 and the normal axis X4. The second plane of angulation A2 is depicted as a line (FIGS. 13 and 15), where the first plane A1 extends orthogonally from the second plane A2. The normal axis X4 falls within the second plane A2, the normal axis X4 being generally parallel the second plane A2. In some embodiments, the force directing member 64 is substantially free to angulate in a single plane of angulation (e.g., the first plane A1) or multiple planes of angulation (e.g., the first plane A1 and the second plane A2) as desired.

In some embodiments, the force directing member 64 is received within the articulation aperture of the adjustment arm 62 such that the force directing member 64 is able to angulate. The force directing member 64 is able to optionally articulate in a first plane of angulation A1 to a greater extent than the force directing member 64 is able to angulate in a second plane of angulation A2 that is substantially perpendicular to the first plane of angulation. In some embodiments, the force directing member 64 has an angulation range of 90 degree, wherein the force directing member 64 is able to articulate through an angle of about 45 degrees or more in the first plane of angulation A1. The force directing member 64 optionally articulates in the first plane of angulation A1 and is substantially prevented from articulating in the second plane of angulation A2. It is also contemplated that the force directing member 64 is able to articulate in a multiple planes of angulation, according to some embodiments.

Figure 17:
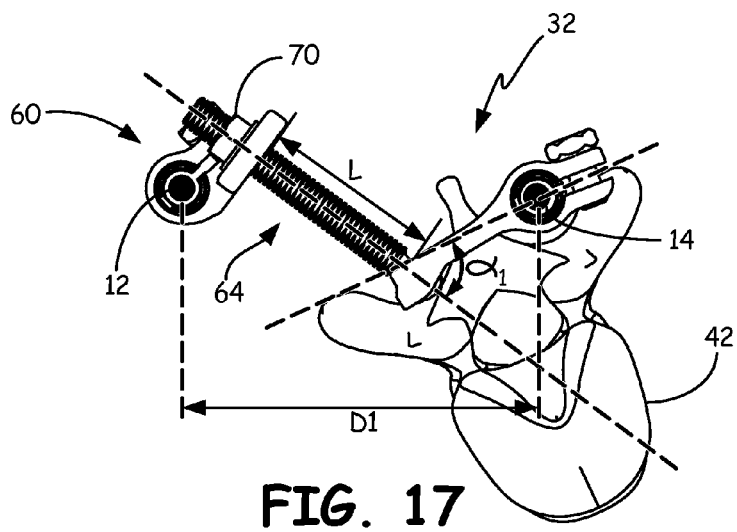
FIGS. 17-19 show the transverse coupler of FIG. 2 at various stages of realignment, according to some embodiments.
Figure 18:
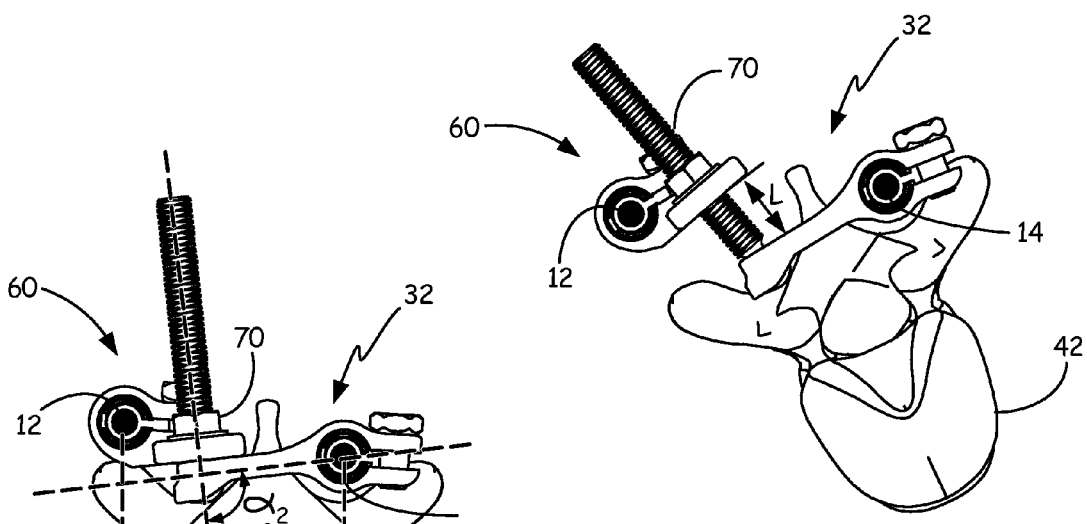
Figure 19:
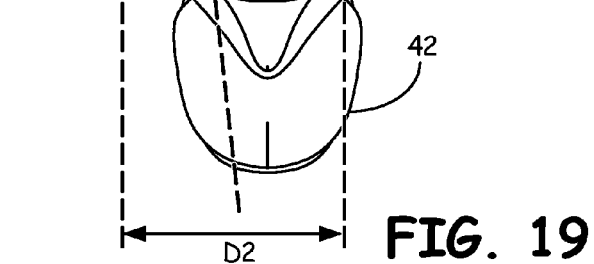

FIGS. 17-19 show a view of the system 10 taken in a transverse plane to the spine 40 near the apex of the defective curvature, with some inferior and superior portions of the spine 40 and system 10 not shown to simplify illustration. As shown, the transverse coupler 32 is secured to the first apical vertebra 42 and to the first and the second rods 12, 14. In sequentially viewing the Figures, it can be seen that during operation, the vertebrae 42 is laterally translated and derotated while the transverse coupler 32 is being adjusted, according to some methods of using the system 10. After the adjustment, the first apical vertebra 42 is then locked against further rotation or lateral movement by locking the transverse coupler 32 to both the first and the second rods 12, 14, according to some embodiments. FIGS. 17 and 18 show the vertebra 42 in an uncorrected state, or a partially derotated and laterally offset state with the first and the second rods 12, 14 secured in first and the second rod couplers 72, 150 of the first transverse coupler 32.

In order to secure the first rod 12 onto the spine 40, the first and second stabilizing anchors 16, 18 are optionally secured at an inferior spinal position, or level, (e.g., to an inferior vertebrae) and a superior spinal position, or level (e.g., to a superior vertebrae), respectively. In some embodiments, the first rod 12 is substantially laterally constrained by the first and second stabilizing anchors 16, 18 such that the first rod 12 extends longitudinally on the first side 40A of the spine 40 and is laterally constrained relative to the inferior and superior vertebrae.

The second rod 14 is optionally secured on an opposite side of the spine at intermediate positions along the spine by a first intermediate anchor and a second intermediate anchor, for example. The first and second intermediate anchors are adapted to substantially constrain the second rod 14 against substantial lateral translation as desired. The first intermediate anchor (e.g., the fifth stabilizing anchor 23 as shown in FIG. 1) is optionally secured to a first, intermediate vertebrae and a second, intermediate vertebrae, each located between the superior and inferior vertebrae to which the first and second stabilizing anchors are secured. In some embodiments, the first and second intermediate anchors are secured to vertebral bodies located on or adjacent vertebral bodies that form an apex, or apical region of the deformity. As shown in FIG. 1, with the spine 40 in a generally corrected state, the first intermediate anchor is positioned at a lower vertebral position, or level than the adjustment assembly 60 and at a higher vertebral position, or level than the first stabilizing anchor 16. In turn, the second intermediate anchor (e.g., the sixth stabilizing anchor 25), is optionally positioned along the spine 40 at a higher vertebral position, or level along the second rod 14 between the adjustment assembly 60 and the second stabilizing anchor 18.

In order to assemble the transverse coupler 32 onto the system 10 (FIG. 1), a physician can optionally articulate components of the transverse coupler 32 (e.g. the force directing member 64 and the adjustment assembly 60), such that the rod couplers 72, 150 of the transverse coupler 32 are able to reach the first and the second rods 12, 14. Alternatively or additionally, a physician or other user can optionally employ a variety of tools and associated methods. For example, the user can optionally use a surigical tool, such as a wrench, clamp, or gripping tool, compressor, distractor adapted to couple to the first rod 12, the second rod 14, the first transverse coupler 32, and/or other spinal devices. The tool is used to assist the physician in derotating and/or translating the spinal column 40 during a correction as desired. The tool is optionally used to assist the physician in maintaining a desired configuration while assembling the system 10 onto the spine 40.

As shown in FIG. 17, the first transverse coupler 32 is assembled onto the first apical vertebra 42. During assembly, the first and the second rod couplers 72, 150 of the first transverse coupler 32 are optionally adjusted to an unlocked state when coupled to the first and the second rods 12, 14 respectively, such that the physician has free movement as desired, when assembling the transverse coupler 32 onto the spine 40. In some embodiments, the first and the second rod couplers 72, 150 are adjusted to an unlocked state to reduce binding of the rods 12, 14 and to provide more degrees of freedom to the first transverse coupler 32 during the lateral translation and derotation of the spine.

During or after assembly, the transverse coupler 32 is optionally adjusted to a locked state onto the rods 12, 14 of the system 10 to allow for lateral translation and derotation of the first apical vertebra 42. In some embodiments, the first and the second rods 12, 14 are generally locked against rotation roll within the corresponding couplers 72, 150 of the first transverse coupler 32, as previously discussed herein. The first rod 12 is optionally left unlocked within the first rod coupler 72 while the second rod 14 is locked against axial translation and changes in pitch and yaw within the second rod coupler 150. In some embodiments, the first rod 12 is able to change in pitch and yaw, while the second rod 14 is substantially constrained against changes in pitch, yaw, and roll during at least a portion of the correction.

In some embodiments, the first rod 12 is able to axially translate and change in pitch and yaw about the first pivot point P1 while the vertebra 42 is being laterally translated and derotated during the full duration of the correction. In other embodiments, the first rod 12 is locked against changes in pitch and yaw during a portion of the correction and/or after the correction. FIGS. 17-19 depict a use of the transverse coupler 32 such that the first rod 12 is able to change in pitch, yaw, and axial translation during a correction and is locked against changes in pitch, yaw, and axial translation after the correction, according to some embodiments.

FIG. 18 shows the first apical vertebra 42 in a partially derotated and a laterally offset state and FIG. 19 shows the first apical vertebra 42 in a maximally derotated and laterally translated state, according to some embodiments. The first transverse coupler 32 operates to laterally translate and rotate the second rod 14 towards the first rod 12 such that a portion of the spine 40 is moved into a more correct configuration, in accordance with some embodiments. For example, comparing FIG. 19 to FIG. 17, it can be seen that the distance between the first rod 12 and the second rod 14 has significantly shortened (identified as D1 and D2 in FIGS. 17 and 15) after the correction. Shown by an arrow in the Figures, the first transverse coupler 32 is optionally adapted to derotate the vertebra 42 and laterally translate the vertebra 42, either contemporaneously, sequentially, or combinations thereof.

FIG. 19 shows the first apical vertebra 42 maximally derotated and laterally translated. The transverse coupler 32 is optionally locked after the vertebra 42 has been laterally translated and derotated as desired (e.g., as shown in FIG. 19), to prevent relative translational and rotational movement between the first rod 12 and second rod 14 to stabilize and hold the vertebra 42 in the corrected position. Additional anchors 23, 25, 28, 30 are added to the spine 40 as desired to provide additional stability to the spine 40. In some embodiments, after the vertebra 42 has been laterally translated and/or partially derotated and the transverse coupler 32 has been locked to the rods, the adjustment retainer 70 is actuated along the force directing member 64 to derotate, or further derotate, the spine 40.

An illustrative but non-limiting example of correcting a spinal defect includes securing the first stabilizing anchor 16 at an inferior spinal position and the second stabilizing anchor 18 at a superior spinal position along the first side 40A of the spine 40. The first rod 12 is extended longitudinally on the first side 40A of the spine 40 and is substantially laterally constrained between the first and the second stabilizing anchors 16, 18, according to some embodiments.

The first anchor 24 is optionally secured at an inferior spinal position and the second anchor 26 is secured at the superior spinal position along the second side 40B of the spine 40. The second rod 14 extends longitudinally on the second side 40B of the spine 40 and is substantially laterally constrained between the first and the second anchors 24, 26, according to some embodiments.

The first transverse coupler 32 is optionally assembled onto the first and the second sides 40A, 40B of the spinal column 40, either at some time prior to, during, or after securing the stabilizing anchors 16, 18, 24, 26 to the spine 40. In some embodiments, the transverse coupler 32 is assembled onto the first side 40A of the spine 40 by coupling the first rod coupler 72 of the adjustment assembly 60 to the first rod 12. The first rod 12 is able to axially translate and change in pitch and yaw, but is substantially restricted from lateral translation at the first rod coupler 72, according to some embodiments.

The transverse coupler 32 is optionally assembled onto the second side 40B of the spine 40 by coupling the second rod coupler 150 of the adjustment arm 62 to the second rod 14. In some embodiments, the second rod 14 is locked from axial translation and changing in pitch, yaw and roll at the second rod coupler 150. The adjustment arm 62 of the first transverse coupler 32 is positioned across the first apical vertebra 42 such that a connecting portion 152 of an adjustment arm 62 extends from the first side 40A of the spine 40 to the second side 40B of the spine 40, according to some embodiments.

As previously discussed, the first transverse coupler 32 includes the force directing member 64 that is optionally the threaded toggle bolt. The force directing member 64 is optionally secured to the adjustment assembly 60 and the adjustment arm 62 with an initial effective length.

In some embodiments, an adjustment retainer 70 is actuated along the force directing member 64 by rotating the threaded cap 130 of the adjustment retainer 70 clockwise along a threaded portion of the force directing member 64. Actuating the retainer 70 decreases the effective length L as desired. In some embodiments, the effective length L becomes approximately zero when the adjustment arm 62 becomes seated flush against the adjustment assembly 60.

The force directing member 64 is optionally cut or broken off to a shorter length, as desired, during the procedure as the effective length L decreases from the initial effective length.

As the adjustment retainer 70 is optionally actuated along the force directing member 64, the rider 66 provides a resistance force that transmits through the force directing member 64 to the adjustment arm 62. In some embodiments, the resistance force causes the second rod 14 to move towards the first rod 12, which laterally translates a portion of the spine 40 towards the first rod 12.

In some embodiments, the adjustment retainer 70 is actuated along the first force directing member 64 such that the first surface 160 of the adjustment arm 62 comes into contact with the adjustment assembly 60. The adjustment retainer 70 is then optionally further actuated to pivot the rider 66 and the adjustment arm 62 towards each other such that the first surface 160 of the adjustment arm 62 becomes seated flush against the second surface 112 of the rider 66. In some embodiments, the adjustment assembly 60 receives the force directing member 64 within an articulation aperture 144 having an elongate transverse cross-section, allowing the force directing member 64 to articulate in the first plane of angulation as the adjustment retainer 70 is driven along the first force directing member 64. As the adjustment assembly 60 and the adjustment arm 62 impinge and ultimately become seated together, the force directing member 64 articulates into a generally orthogonal angle relative to the longitudinal axis X3 defined by the adjustment arm 62, according to some embodiments. In some embodiments, as the force directing member 64 articulates, the first apical vertebra 42 derotates. Once the adjustment arm 62 and the adjustment assembly 60 are brought into the desired amount of contact or the desired effective length L of the force directing member 64 has been achieved.

Figure 20:
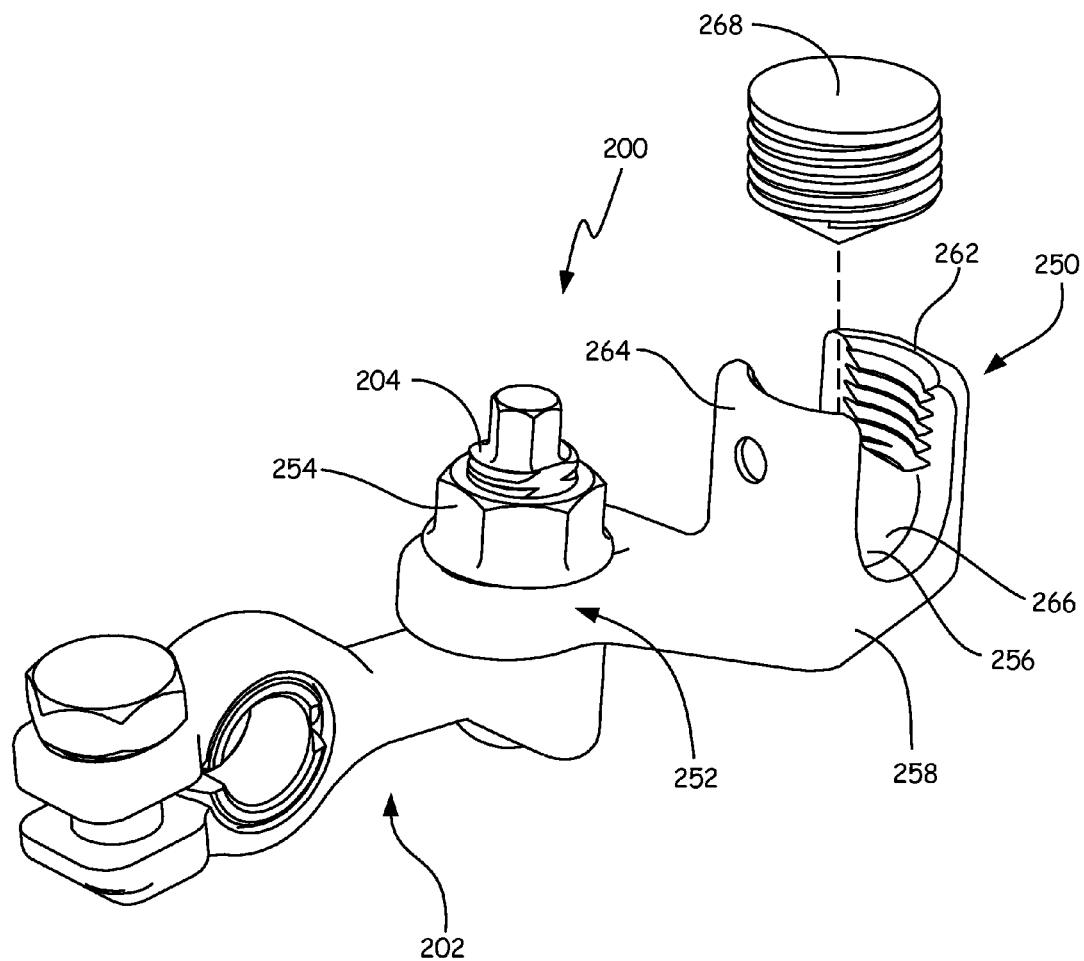
FIG. 20 is an isometric view of an alternative embodiment of a transverse coupler of the system of FIG. 1, according to some embodiments.

FIG. 20 shows an isometric view of an alternative embodiment of a first transverse coupler 200 of the system 10, also described as a transverse connector. The first transverse coupler 200 is optionally adapted, or otherwise structured, to be positioned laterally across one or more of the vertebrae, such as the first apical vertebra 42 (FIG. 1) located at or near an apical position along the spine 40. As shown, the first transverse coupler 200 is adapted to extend from the first side 40A of the spine 40 toward, and ultimately across to the second side 40B of the spine 40.

As shown, the first transverse coupler 200 includes features that are substantially similar to the first transverse coupler 32. In some embodiments, the adjustment arm 202 is substantially similar to the adjustment arm 62 of the first transverse coupler 32, and thus various features of the adjustment arm 62 of the first transverse coupler 32 also apply to the adjustment arm 202 of the first transverse coupler 200.

As shown in FIG. 20, the first transverse coupler 200 includes an adjustment assembly 250 adapted to be secured to a first rod 12. In some embodiments, the adjustment assembly 250 includes a rider 252, an adjustment retainer 254, and a first rod coupler 256 to receive the first rod 12.

Figure 21:
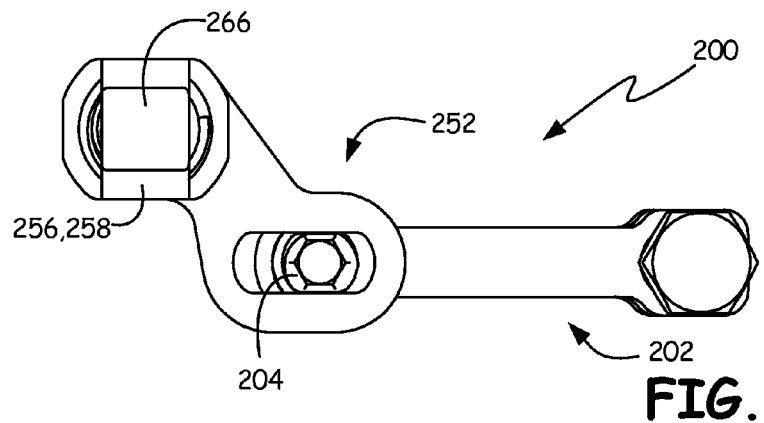
FIGS. 21-23 show top, side, and a rear views, respectively, of the transverse coupler of FIG. 20, according to some embodiments.
Figure 22:
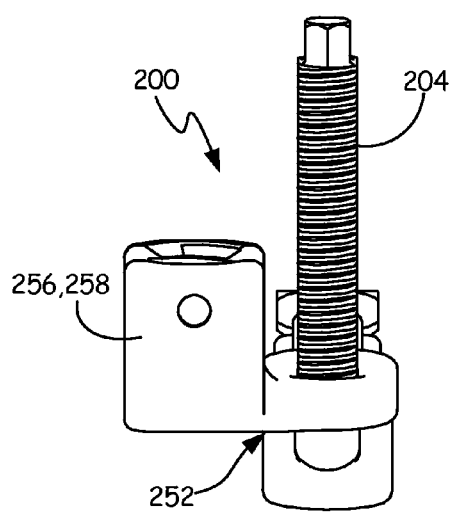
Figure 23:
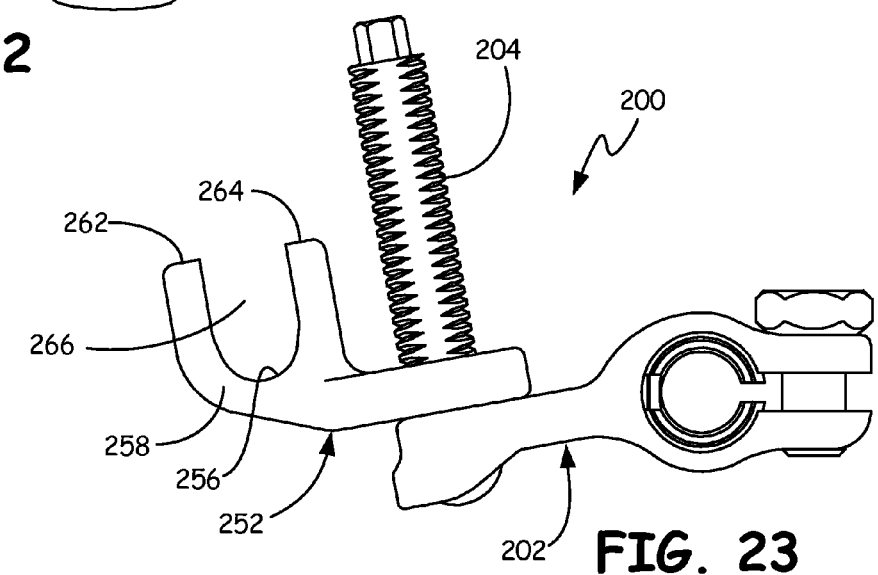

FIGS. 21-23 show a top, a side and a rear view of the first transverse coupler 200. In some embodiments, the rider 252 and the adjustment retainer 254 of the first transverse coupler 200 engage with an adjustment arm 202 and/or a force directing member 204 in a manner substantially similar to the rider 66 and adjustment retainer 70 of the first transverse coupler 32. The various features of the rider 66 and the adjustment retainer 70 of the first transverse coupler 32 also apply to the rider 252 and the adjustment retainer 254 of the first transverse coupler 200. The main difference between the first transverse coupler 200 and the first transverse coupler 32 is the first rod coupler 256, according to some embodiments.

As shown in FIGS. 20 and 23, the first rod coupler 256 includes a head portion 258 is substantially U-shaped having a first prong 262 and a second prong 264 defining a pocket 266 for receiving the first rod 12. The head portion 258 of the adjustment assembly 250 serves to couple the first transverse coupler 200 to the first rod 12. As shown, the prongs 262, 264 are threaded for receiving a clamping screw 268 adapted to engage and secure the first rod 12 immobilized within the pocket 266. The first rod coupler 256 of the adjustment assembly 250 is optionally configured to receive the first rod 12 such that the first rod 12 is free to change in at least roll within the first rod coupler 256. In some embodiments, first rod coupler 256 is configured to receive the first rod 12 such that the first rod 12 is free to change in pitch and roll, but is substantially limited from changes in yaw within the first rod coupler 256. In some embodiments, the first rod coupler 256 is configured to be transitioned from an unlocked state in which the first rod 12 is free to move in at least one of slide, pitch, yaw or roll with respect to the first rod coupler 256 to a locked state. In some embodiments, the first rod 12 is received by the first rod coupler 256 such that the first rod coupler 256 becomes substantially laterally constrained by the first rod 12. The first rod coupler 256 optionally locks the first rod 12 against axial translation, changes in pitch, yaw and roll about a rod pivot point with respect to the first rod coupler 256.

Figure 24:
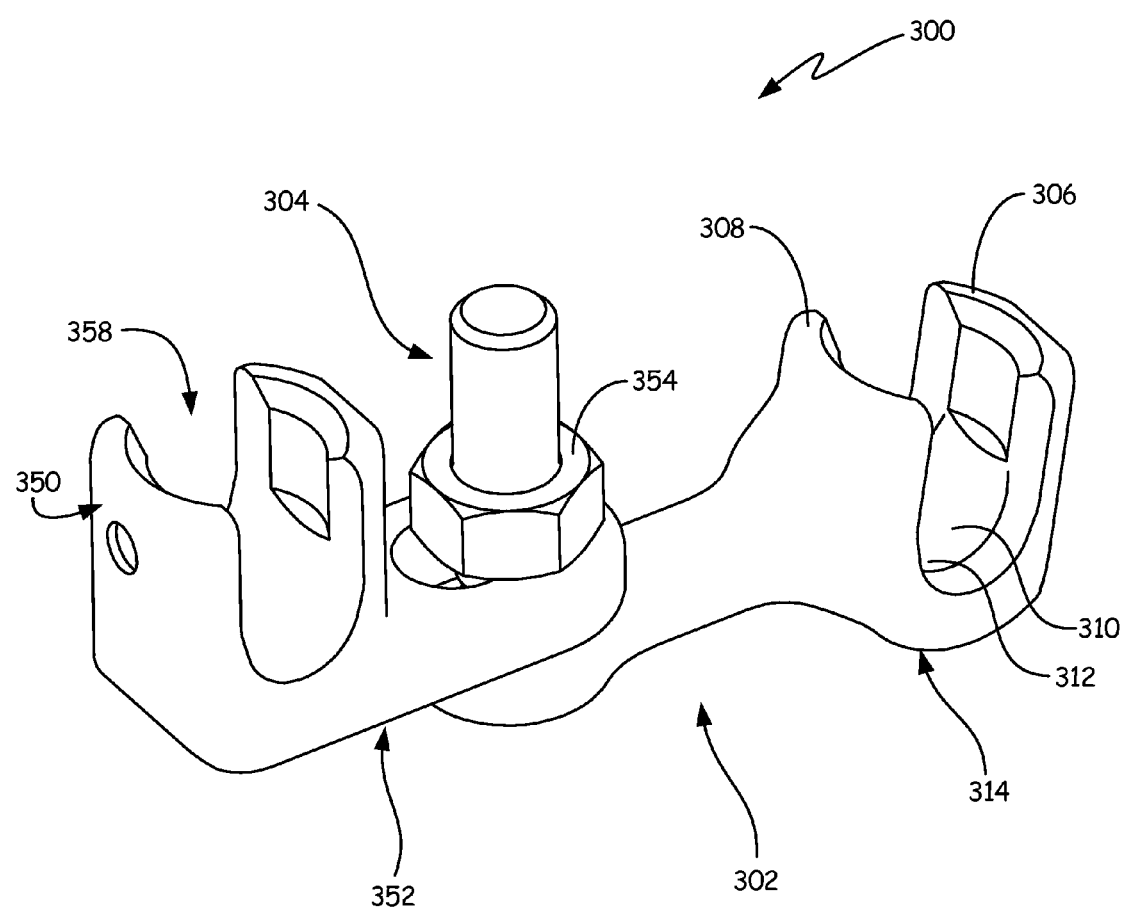
FIG. 24 is an isometric view of an alternative embodiment of a transverse coupler of the system of FIG. 1, according to some embodiments.

FIG. 24 provides another alternative embodiment of the first transverse coupler 300, which includes an adjustment assembly 350 adapted to be secured to a first rod 12. In some embodiments, the adjustment assembly 350 includes a rider 352, an adjustment retainer 354, and a first rod coupler 358 to receive the first rod 12. The first rod coupler 358 optionally receives the first rod 12 in a substantially similar manner to the adjustment assembly 250 of the first transverse coupler 200, and therefore various features of the adjustment assembly 250 of the first transverse coupler 200 also apply to the adjustment assembly 350 of the first transverse coupler 300. The primary difference between the first transverse coupler 300 and the first transverse coupler 200 is the design of the second rod coupler 312 of the adjustment arm 302, according to some embodiments.

As shown in FIG. 24, the adjustment arm 302 is substantially similar to the adjustment arm 62 of the first transverse coupler 32 with a difference of having a second rod coupler 312 that includes a U-shaped head portion 314. The head portion 314 is substantially U-shaped and includes a first prong 306 and a second prong 308 that defines a pocket 310 for receiving the second rod 14. The head portion 314 of the adjustment arm 302 serves to couple the first transverse coupler 300 to the second rod 14. As shown, the prongs 306, 308 are optionally threaded for receiving a clamping screw (not shown) adapted to engage and secure the second rod 14 immobilized within the pocket 310. The second rod coupler 312 receives the second rod 14 similar to how the first coupler 356 receives the second rod 14, and therefore those various features of the first rod coupler 256 are also applicable to the second rod coupler 312 with respect to the second rod 14.

FIG. 25 shows an isometric view of another first transverse coupler 400 of the system 10, also described as a fixed transverse coupler. The first transverse coupler 400 is optionally adapted, or otherwise structured, to be positioned laterally across one or more of the vertebrae, such as the first apical vertebra 42 (FIG. 1) located at or near an apical position along the spine 40. As shown, the first transverse coupler 200 is adapted to extend from the first side 40A of the spine 40 toward, and ultimately across to the second side 40B of the spine 40.

As shown, the first transverse coupler 400 includes features that are substantially similar to the first transverse coupler 32. In some embodiments, the first transverse coupler 400 includes an adjustment assembly 450 adapted to be secured to a first rod 12. In some embodiments, the adjustment assembly 450 includes a rider 452, an adjustment retainer 454, and a first rod coupler 456 to receive the first rod 12. In some embodiments, the adjustment assembly 450 is substantially similar to the adjustment assembly 60 of the first transverse coupler 32.

The first transverse coupler 400 optionally includes an adjustment arm 402 with a second rod coupler 412 adapted to be secured to the second rod 14 and extends from the first side 40A of the spine 40 to the second side 40B of the spine 40. In some embodiments, the adjustment arm 402 has a first end 406 and a second end 408 and a longitudinal axis X3 extending between the first and the second ends 406, 408. The adjustment arm 402 optionally has a first surface 414 and a second opposite surface 416 (FIG. 26).

FIG. 26 shows a view of the adjustment arm 402, with some features not shown to facilitate understanding, which is substantially similar to the adjustment arm 62 of the first transverse coupler 32 with a difference of having a force directing member 404 rigidly secured to the first end 406 of the adjustment arm 402. In some embodiments, the force directing member 404 extends from the first surface 414 of the adjustment arm 402 at a generally orthogonal angle relative to the longitudinal axis X3. In other embodiments, the force directing member 404 extends from the first surface 414 of the adjustment arm 402 at a non-orthogonal angle relative to the longitudinal axis X3. The force directing member 404 has an elongate body 410 extending between the adjustment assembly 450 and the adjustment arm 402, according to some embodiments.

The adjustment arm 402 optionally includes an elongated portion 418 with an aperture 420 at the first end 406 of the adjustment arm 402. The aperture 420 is optionally adapted to receive at least a portion of a surgical tool that may be used during the implant procedure to obtain and hold a spinal correction.

FIGS. 27-29 show a view of the system 10 taken in a transverse plane to the spine 40 near the apex of the defective curvature, with some inferior and superior portions of the spine 40 and system 10 not shown to simplify illustration. As shown, the transverse coupler 400 is secured to the first apical vertebra 42 and to the first and the second rods 12, 14. In sequentially viewing the Figures, it can be seen that during operation, the first apical vertebra 42 is laterally translated and derotated while the transverse coupler 400 is being adjusted, according to some methods of using the system 10. FIGS. 27 and 28 show the first apical vertebra 42 in a partially derotated and a laterally offset state and FIG. 29 shows the first apical vertebra 42 maximally derotated and laterally translated.

In order to assemble the transverse coupler 400 onto the system 10 (FIG. 1), a physician can optionally angulate the adjustment assembly 450 of the transverse coupler 200 (e.g.) such that the rod couplers 456, 412 of the transverse coupler 400 are able to reach the first and the second rods 12, 14. Alternatively or additionally, a physician or other user can optionally employ a variety of tools and associated methods. For example, the user can use a surgical tool, such as a wrench, clamp, or gripping tool, adapted to couple to the first rod 12, the second rod 14, the first transverse coupler 400, and/or other spinal devices as desired. In some embodiments, the surgical tool optionally assists the physician in derotating and/or translating a spinal column 40 during a correction. The surgical tool optionally assists the physician in maintaining a desired configuration while assembling the system 10 onto the spine 40.

A spinal correction using the first transverse coupler 200 as shown in FIGS. 27-29 optionally proceeds similarly to the spinal correction using the transverse coupler 32 as shown in FIGS. 13-16.

An illustrative but non-limiting example of correcting a spinal defect using the first transverse coupler 400 is provided herein. Stabilizing anchors 16, 18, anchors 24, 26, and rods 12, 14 are optionally secured to the spine 40 using the operation as discussed previously.

The first transverse coupler 200 is assembled onto the first and the second sides 40A, 40B of the spinal column 40, either at some time prior to, during, or after securing the stabilizing anchors 16, 18, 24, 26 to the spine 40. In some embodiments, the transverse coupler 400 is assembled onto the first side 40A of the spine 40 by coupling the first rod coupler 456 of the adjustment assembly 250 to the first rod 12. The first rod 12 is able to axially translate and change in pitch and yaw, but is substantially restricted from translating laterally at the first rod coupler 456, according to some embodiments.

The transverse coupler 400 is optionally assembled onto the second side 40B of the spine 40 by coupling the second rod coupler 412 of the adjustment arm 402 to the second rod 14. In some embodiments, the second rod 14 is locked from axial translation and changing in pitch, yaw and roll at the second rod coupler 412. The adjustment arm 402 of the first transverse coupler 400 is be positioned across the first apical vertebra 42 such that a connecting portion 422 of an adjustment arm 402 extends from the first side 40A of the spine 40 to the second side 40B of the spine 40, according to some embodiments.

As previously discussed, the first transverse coupler 400 optionally has the force directing member 404 rigidly coupled to the adjustment arm 402. In some embodiments, the adjustment retainer 454 is actuated along the force directing member 404 by rotating a threaded cap 455 of the adjustment retainer 454 clockwise along a threaded portion of the force directing member 404. Actuating the adjustment retainer 454 decreases an effective length L (FIG. 27) of the force directing member 404 as desired. In some embodiments, the effective length L becomes approximately zero when the adjustment arm 402 becomes seated flush against the adjustment assembly 450. In other words, actuating the retainer 454 optionally changes the distance and orientation of the rider 452 with respect to the adjustment arm 402. In some embodiments, actuating the retainer 454 optionally couples the rider 452 to the adjustment arm 402. The force directing member 404 is optionally cut or broken off to a shorter length, as desired, during the procedure as the effective length L decreases from the initial effective length.

As the adjustment retainer 454 is optionally actuated along the force directing member 404, the rider 452 provides a resistance force that transmits through the force directing member 404 to the adjustment arm 402. In some embodiments, the resistance force causes the second rod 14 to move towards the first rod 12, which laterally translates a portion of the spine 40 towards the first rod 12.

In some embodiments, the adjustment retainer 454 is actuated along the first force directing member 404 such that the first surface 414 of the adjustment arm 402 comes into contact with the adjustment assembly 450. The adjustment retainer 454 is then optionally further actuated to pivot the rider 452 and the adjustment arm 402 towards each other such that the first surface 414 of the adjustment arm 402 becomes seated flush against a second surface 460 of the rider 452. As the adjustment assembly 450 and the adjustment arm 402 impinge and ultimately become seated together, according to some embodiments. Once the adjustment arm 402 and the adjustment assembly 450 are brought into the desired amount of contact or the desired effective length L of the force directing member 404 has been achieved.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A transverse coupler for a spinal correction system, the transverse coupler comprising:
    an adjustment assembly configured to be secured to a first rod extending longitudinally along a first side of a spine, the adjustment assembly including a rider, a retainer, and a first rod coupler, the first rod coupler configured to receive the first rod such that the first rod is free to translate axially through the first rod coupler, pivot in pitch and yaw at the first rod coupler, and roll within the first rod coupler;
    an adjustment arm configured to be secured to a second rod extending longitudinally along a second side of a spine and to be extended from a second side of a spine toward a first side of a spine, the adjustment arm defining a first end, a second end, a first surface, a second surface, and a longitudinal axis extending from the first end to the second end;
    a force directing member with an elongate body configured to couple with the rider and the first end of the adjustment arm, the rider and the elongate body being configured to form a complementary fit, wherein the rider can move along the elongate body and couple with the adjustment arm at a plurality of angles;
    a first intermediate anchor adapted to be positioned along the second rod between the adjustment arm and a first stabilizing anchor; and
    a second intermediate anchor adapted to be positioned along the second rod between the adjustment arm and a second stabilizing anchor,
    wherein each of the first and second intermediate anchors is adapted to substantially constrain the second rod against substantial lateral translation.

2. The transverse coupler of claim 1, wherein the retainer of the adjustment assembly is configured to couple to and move along the elongate body of the force directing member such that a distance and an orientation of the rider changes with respect to the adjustment arm and the rider can couple with the adjustment arm.

3. The transverse coupler of claim 1, wherein the elongate body has a threaded portion and the retainer includes a threaded cap configured to mate with the threaded portion of the elongate body.

4. The transverse coupler of claim 1, wherein the force directing member is a post and the rider includes a slot with a top surface and bottom surface such that the slot is configured to receive the force directing member.

5. The transverse coupler of claim 1, wherein the adjustment arm includes an aperture in the first end extending from the first surface to the second surface, the aperture being adapted to receive the force directing member such that the force directing member is free to angulate with respect to the first surface.

6. The transverse coupler of claim 5, wherein the first surface of the adjustment arm is configured to engage with the rider and the force directing member extends from the first surface of the adjustment arm at an adjustable angle relative to the longitudinal axis, the adjustable angle ranging from 0 to 90 degrees.

7. The transverse coupler of claim 1, wherein the force directing member is rigidly secured to the first end of the adjustment arm and extends from the first surface of the adjustment arm at a substantially fixed angle relative to the longitudinal axis.

8. The transverse coupler of claim 7, wherein the force directing member extends from the first surface of the adjustment arm at a substantially orthogonal angle relative to the longitudinal axis.

9. The transverse coupler of claim 1, wherein the first rod coupler of the adjustment assembly is configured to receive the first rod such that the first rod is free to change in at least roll within the first rod coupler.

10. The transverse coupler of claim 1, wherein the first rod coupler includes a sleeve insert forming a revolute, substantially convex articulation surface and a body that forms a substantially concave articulation surface for receiving the sleeve insert.

11. The transverse coupler of claim 1, wherein the first rod coupler is configured to be transitioned from an unlocked state in which the first rod is free to move in at least one of axial translation, pitch, yaw or roll with respect to the first rod coupler to a locked state in which the first rod received by the first rod coupler is substantially laterally constrained and locked against axial translation, changes in pitch and yaw about a rod pivot point, and roll with respect to the first rod coupler.

12. The transverse coupler of claim 1, wherein the second end of the adjustment arm is configured to be secured to an anchor point on a second side of a spine where the anchor point includes a second rod coupler configured to be secured to the second rod.

13. The transverse coupler of claim 12, wherein of the second rod coupler of the adjustment arm is configured to be substantially laterally constrained by the second rod received by the second rod coupler.

14. The transverse coupler of claim 13, wherein the second rod coupler defines a rod pivot point and is configured to be transitioned from an unlocked state in which the second rod received by the second rod coupler is free to move in at least one of axial translation, pitch, yaw or roll about the rod pivot point to a locked state in which the second rod received by the second rod coupler is substantially laterally constrained and locked against axial translation and changes in pitch and yaw about the rod pivot point with respect to the second rod coupler.

15. The transverse coupler of claim 12, wherein the adjustment assembly and the adjustment arm are configured to be transitioned from an unlocked state in which the first rod is free to move in at least one of axially translate, pitch, yaw or roll with respect to the anchor point on the second side of the spine to a locked state in which the first rod is substantially laterally constrained and locked against axial translation, changes in pitch and yaw about the rod pivot point, and roll with respect to the anchor point on the second side of the spine.

16. A transverse coupler for a spinal correction system, the transverse coupler comprising:
    an adjustment assembly configured to be secured to a first rod extending longitudinally along a first side of a spine, the adjustment assembly including a rider, a retainer, and a first rod coupler;
    an adjustment arm configured to be secured to a second rod extending longitudinally along a second side of a spine and to be extended from a second side of a spine toward a first side of a spine, the adjustment arm defining a first end, a second end, a first surface, a second surface, and a longitudinal axis extending from the first end to the second end; and
    a force directing member with an elongate body configured to couple with the rider and the first end of the adjustment arm, the rider and the elongate body being configured to form a complementary fit, wherein the rider can move along the elongate body and couple with the adjustment arm at a plurality of angles,
    wherein the adjustment arm includes an aperture in the first end extending from the first surface to the second surface, the aperture being adapted to receive the force directing member such that the force directing member extends from the first surface of the adjustment arm and is free to angulate with respect to the first surface.

17. A transverse coupler for a spinal correction system, the transverse coupler comprising:
    an adjustment assembly configured to be secured to a first rod extending longitudinally along a first side of a spine, the adjustment assembly including a rider, a retainer, and a first rod coupler;
    an adjustment arm configured to be secured to a second rod extending longitudinally along a second side of a spine and to be extended from a second side of a spine toward a first side of a spine, the adjustment arm defining a first end, a second end, a first surface, a second surface, and a longitudinal axis extending from the first end to the second end; and
    a force directing member with an elongate body configured to couple with the rider and the first end of the adjustment arm, the rider and the elongate body being configured to form a complementary fit, wherein the rider can move along the elongate body and couple with the adjustment arm at a plurality of angles,
    wherein the force directing member is rigidly secured to the first end of the adjustment arm and extends from the first surface of the adjustment arm at a substantially fixed acute angle relative to the longitudinal axis.

* * * * *